United States Patent
Cerny et al.

(10) Patent No.: US 10,622,107 B2
(45) Date of Patent: Apr. 14, 2020

(54) TOOLS FOR MEDICAL DEVICE CONFIGURATION

(71) Applicant: Medtronic, Inc., Minneapolis, MN (US)

(72) Inventors: Douglas S. Cerny, Minneapolis, MN (US); Raj Mehra, Savage, MN (US); Michael Cullen-Benson, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 674 days.

(21) Appl. No.: 15/044,837

(22) Filed: Feb. 16, 2016

(65) Prior Publication Data

US 2016/0239627 A1 Aug. 18, 2016

Related U.S. Application Data

(60) Provisional application No. 62/115,834, filed on Feb. 13, 2015.

(51) Int. Cl.
*G16H 40/40* (2018.01)
*A61N 1/372* (2006.01)
(Continued)

(52) U.S. Cl.
CPC .......... *G16H 40/40* (2018.01); *A61M 5/142* (2013.01); *A61N 1/0534* (2013.01);
(Continued)

(58) Field of Classification Search
CPC .. G06F 19/3412; G06F 3/0482; G06F 3/0486; G06F 2203/04803; G06F 19/3481;
(Continued)

(56) References Cited

U.S. PATENT DOCUMENTS 5,949,998 A * 9/1999 Fowlow .................... G06F 8/34
717/103
6,393,325 B1 * 5/2002 Mann ................. A61N 1/36071
607/46

(Continued)

FOREIGN PATENT DOCUMENTS

WO 2014139019 A1 9/2014

OTHER PUBLICATIONS

Mikos et al., "Patient-Specific Analysis of the Relationship Between the Volume of Tissue Activated During DBS and Verbal Fluency," National Institutes of Health, Jan. 2011, 20 pp.

*Primary Examiner* — Ajay M Bhatia
*Assistant Examiner* — Phoebe X Pan
(74) *Attorney, Agent, or Firm* — Shumaker & Sieffert, P.A.

(57) ABSTRACT

An example method includes presenting, by a computing device, via a user interface (UI), a representation of the medical device and respective representations of one or more components that are attachable to the medical device, wherein the one or more components comprise at least one of leads, adaptors, extensions, or catheters, receiving, by the computing device, via the UI, an indication of a selected component included in the component(s) for attachment to the medical device, and responsive to receiving the indication of the selected component: indicating, by the computing device and via the UI, attachment of the representation of the selected component to the representation of the medical device, and updating, by the computing device, the presentation of the respective representations of the component(s) via the UI to include representations of one or more components that are attachable to the medical device with the selected component.

32 Claims, 12 Drawing Sheets

(51) Int. Cl.
*A61N 1/05* (2006.01)
*G06F 3/0482* (2013.01)
*G06F 3/0486* (2013.01)
*A61M 5/142* (2006.01)
*A61N 1/36* (2006.01)
*A61M 39/10* (2006.01)
*G06F 19/00* (2018.01)

(52) U.S. Cl.
CPC ....... *A61N 1/0551* (2013.01); *A61N 1/36142* (2013.01); *A61N 1/37247* (2013.01); *G06F 3/0482* (2013.01); *G06F 3/0486* (2013.01); *G06F 19/00* (2013.01); *A61M 2039/1005* (2013.01); *A61M 2039/1077* (2013.01); *A61M 2205/502* (2013.01); *G06F 2203/04803* (2013.01)

(58) Field of Classification Search
CPC .... G06F 19/34; G06F 19/325; G06F 19/3418; G06F 3/0484; G06F 3/04842; A61M 5/142; A61M 2039/1005; A61M 2039/1077; A61M 2205/502; A61N 1/0534; A61N 1/0551; A61N 1/37247
See application file for complete search history.

(56) References Cited

U.S. PATENT DOCUMENTS

| | | | |
|---|---|---|---|
| 6,725,257 B1* | 4/2004 | Cansler | G06Q 10/087 709/203 |
| 7,491,198 B2 | 2/2009 | Kockro | |
| 7,657,319 B2 | 2/2010 | Goetz et al. | |
| 7,831,294 B2 | 11/2010 | Viswanathan | |
| 8,121,694 B2 | 2/2012 | Molnar et al. | |
| 8,341,176 B1* | 12/2012 | Rabsatt | G06Q 30/0603 707/767 |
| 8,532,741 B2 | 9/2013 | Heruth et al. | |
| 8,649,845 B2 | 2/2014 | McIntyre et al. | |
| 8,660,653 B2 | 2/2014 | Kothandaraman et al. | |
| 8,862,240 B2 | 10/2014 | Goetz et al. | |
| 8,918,177 B2 | 12/2014 | Gauthier | |
| 9,652,561 B2* | 5/2017 | Sato | G06F 16/907 |
| 9,895,545 B2* | 2/2018 | Rao | A61N 1/37247 |
| 2004/0215089 A1* | 10/2004 | Bergelson | A61B 5/0006 600/510 |
| 2009/0177081 A1 | 7/2009 | Joskowicz et al. | |
| 2009/0281595 A1* | 11/2009 | King | A61N 1/0553 607/46 |
| 2009/0287271 A1* | 11/2009 | Blum | G16H 50/50 607/45 |
| 2010/0332350 A1* | 12/2010 | Rinehart | G06Q 30/0603 705/27.2 |
| 2011/0093051 A1* | 4/2011 | Davis | A61N 1/372 607/116 |
| 2011/0172737 A1* | 7/2011 | Davis | A61N 1/36071 607/59 |
| 2011/0282414 A1 | 11/2011 | Kothandaraman et al. | |
| 2012/0029598 A1* | 2/2012 | Zhao | A61B 5/0031 607/60 |
| 2012/0083857 A1* | 4/2012 | Bradley | A61N 1/36175 607/46 |
| 2012/0100517 A1 | 4/2012 | Bowditch et al. | |
| 2012/0265269 A1* | 10/2012 | Lui | A61N 1/37247 607/46 |
| 2013/0038707 A1 | 2/2013 | Cunningham et al. | |
| 2013/0060299 A1* | 3/2013 | Polefko | A61N 1/36017 607/46 |
| 2013/0060300 A1* | 3/2013 | Polefko | A61N 1/36017 607/46 |
| 2013/0060301 A1* | 3/2013 | Polefko | A61N 1/36017 607/46 |
| 2013/0060302 A1* | 3/2013 | Polefko | A61N 1/36017 607/46 |
| 2013/0088582 A1 | 4/2013 | Moinzadeh | |
| 2013/0323700 A1 | 12/2013 | Samosky et al. | |
| 2014/0025343 A1* | 1/2014 | Gregg | G06F 17/5004 703/1 |
| 2014/0062900 A1 | 3/2014 | Kaula et al. | |
| 2014/0067011 A1* | 3/2014 | Kaula | A61N 1/37247 607/59 |
| 2014/0067016 A1* | 3/2014 | Kaula | A61N 1/37247 607/59 |
| 2014/0067019 A1* | 3/2014 | Kothandaraman | A61N 1/36185 607/60 |
| 2014/0067020 A1* | 3/2014 | Kaula | A61N 1/37247 607/60 |
| 2014/0081127 A1 | 3/2014 | Patil et al. | |
| 2014/0163639 A1 | 6/2014 | Zhu | |
| 2014/0200633 A1 | 7/2014 | Moffitt | |
| 2014/0249599 A1* | 9/2014 | Kaula | A61N 1/36071 607/46 |
| 2015/0142600 A1* | 5/2015 | Muthyala | G06Q 30/0603 705/26.5 |
| 2017/0185953 A1* | 6/2017 | Dalforno | G06Q 10/087 |

* cited by examiner

TOOLS FOR MEDICAL DEVICE CONFIGURATION

This application claims the benefit of U.S. Provisional Application No. 62/115,834, filed on 13 Feb. 2015, the entire contents of which are incorporated herein by reference.

TECHNICAL FIELD

The disclosure generally relates to configuring medical devices, and in some specific examples, relates to specifying, via an interactive user interface, the configuration of a medical device including one or more components connectable to the medical device.

BACKGROUND

Implantable medical devices, such as electrical stimulators or fluid delivery pumps, may be used to deliver therapy to patients to alleviate any of a variety of symptoms or conditions. Electrical stimulators, for example, may be used to deliver electrical stimulation therapy to patients to treat a variety of symptoms or conditions such as chronic pain, tremor, Parkinson's disease, epilepsy, urinary or fecal incontinence, sexual dysfunction, obesity, or gastroparesis. In general, an implantable stimulator may deliver stimulation therapy (e.g., neurostimulation therapy) in the form of electrical pulses or continuous waveforms. An implantable stimulator may deliver stimulation therapy via one or more leads that include electrodes located proximate to target locations associated with the brain, the spinal cord, pelvic nerves, peripheral nerves, or the gastrointestinal tract of a patient. Hence, stimulation may be used in different therapeutic applications, such as deep brain stimulation (DBS), spinal cord stimulation (SCS), pelvic stimulation, gastric stimulation, or peripheral nerve stimulation. Stimulation also may be used for muscle stimulation, e.g., functional electrical stimulation (FES), to promote muscle movement or prevent atrophy.

SUMMARY

In general, the disclosure is directed to techniques that enable users to specify the configuration of medical devices, such as implantable electrical stimulators and/or implantable drug pumps. Specifying the configuration of medical devices may include, for example, identifying components used to construct the medical devices, and their connections. Aspects of this disclosure are directed to providing user interface (UI)-based menus and workspaces, with which a user (e.g., a clinician) may specify the configuration of a medical device.

For example, a user, such as a clinician, builds and/or configures an implantable electrical stimulator using different types of leads, adapters, and extensions. As used herein, an "electrical stimulator" may refer to a stimulation system that includes a stimulation controller (or "can"), one or more leads and (optionally) one or extensions and/or adapters. Different types of leads may have, for example, different numbers or arrangements of electrodes. By building and configuring the implantable stimulator in this way, the clinician may customize the therapy to be delivered by the implantable stimulator. For example, the clinician may select from various types of leads, and may form various combinations of leads of the same or different type, to build the implantable stimulator. By constructing implantable stimulators according to different configurations, the clinician may customize the contact points (e.g., implemented using electrodes of the leads) at which the implantable stimulator delivers electrical stimulation to the patient. Additionally, the clinician may use various adaptors and/or extensions to mix and match leads that would otherwise be incompatible. Nevertheless, different stimulation controllers may only be capable of supporting certain numbers of electrodes, and certain combinations of leads, extensions, and adapters.

According to various implementations, this disclosure is directed to an interactive UI-based tool that enables a clinician to select from a predetermined subset of possible leads, extensions, and adapters to attach to a stimulation controller or "can" of an implantable stimulator. The predetermined subset presented to the clinician may depend on previous component selections. For example, systems and techniques of this disclosure may provide an interactive tool that displays a selection of leads that are compatible with a particular stimulation controller. The stimulation controller may represent a "fixed" portion of the configuration process, while the leads may represent a "variable" portion, in that the clinician can select different combinations and permutations of leads with respect to a single stimulation controller. In some instances, the interactive tool may provide options for various adapters and/or extensions, thereby enabling the clinician to mix and match among a greater variety of lead types, such that the interactive representation of the electrical stimulator is able to reflect the full range of electrical stimulator options available to the clinician.

In some implementations, the interactive tool may be dynamically updated. For instance, the interactive tool may change lead options (as well as options for adapters and/or extensions) in response to prior selections or edits performed by the clinician. As one example, if the clinician attaches (or "snaps on") a particular lead representation to a representation of particular stimulation controller using the interactive tool, the interactive tool may dynamically adjust the listing of available options to include only those leads, adapters, and extensions that are compatible with stimulation controller and the already-attached lead. Conversely, if the clinician detaches (or "unsnaps") any previously-attached lead representation(s) from the stimulator representation, the interactive tool may repopulate the listed options that were removed due to incompatibility with the combination of the stimulator and the now-detached lead(s).

In some examples, this disclosure is directed to a method for configuring a representation of a medical device. The method includes presenting, by a computing device, via a user interface (UI), a representation of the medical device and respective representations of one or more components that are attachable to the medical device, wherein the one or more components comprise at least one of leads, adaptors, extensions, or catheters. The method further includes receiving, by the computing device, via the UI, an indication of a selected component included in the one or more components for attachment to the medical device. The method further includes, responsive to receiving the indication of the selected component: indicating, by the computing device and via the UI, attachment of the representation of the selected component to the representation of the medical device, and updating, by the computing device, the presentation of the respective representations of the one or more components via the UI to include representations of one or more components that are attachable to the medical device with the selected component.

In some examples, this disclosure is directed to a programming device for a medical device that includes a communication module configured to communicate with the medical device, a memory, a user interface (UI) configured to receive inputs and to output data, and one or more processors. The one or more processors are configured to present, via the UI, a representation of the medical device and respective representations of one or more components that are attachable to the medical device, wherein the one or more components comprise at least one of leads, adaptors, extensions, or catheters. The one or more processors are further configured to receive, via the UI, an indication of a selected component included in the one or more components for attachment to the medical device. The one or more processors are further configured to, responsive to receiving the indication of the selected component: indicate, via the UI, attachment of the representation of the selected component to the representation of the medical device, and to update the presentation of the respective representations of one or more components via the UI to include representations of one or more components that are attachable to the medical device with the selected component.

In some examples, this disclosure is directed to a system that includes a medical device configured to deliver one or both of electrical signals or one or more therapeutic agents, and a programming device configured to communicate with the medical device. The programming device includes one or more processors. The processors(s) of the programming device are configured to present, via a user interface (UI), a representation of the medical device and respective representations of one or more components that are attachable to the medical device, wherein the one or more components comprise at least one of leads, adaptors, extensions, or catheters, and to receive, via the UI, an indication of a selected component included in the one or more components for attachment to the medical device. The processor(s) of the programming device are further configured to, responsive to receiving the indication of the selected component: indicate, via the UI, attachment of the representation of the selected component to the representation of the medical device, and to update the presentation of the respective representations of one or more components via the UI to include representations of one or more components that are attachable to the medical device with the selected component.

In various examples, the configuration may match the physical configuration already selected by a clinician, or may help the clinician plan a configuration. Once a configuration is selected, the clinician may use the interactive tool to customize programming options for setting stimulation parameters such as amplitude, pulse width, pulse rate, electrode polarity, and electrode combination to correspond to the features of the selected configuration. The programming options may be customized based on, or tailored to, the configurations selected by the clinician. For example, if an eight-electrode lead is already selected, then the interactive tool may present programming options for delivering stimulation using selected combinations of the eight electrodes, rather than four electrodes or sixteen electrodes (which would not match the configuration selected via the user interface).

Details of one or more examples are set forth in the accompanying drawings and the description below. Other features, objects, and advantages will be apparent from the description and drawings, and from the claims.

DETAILED DESCRIPTION

Figure 1:
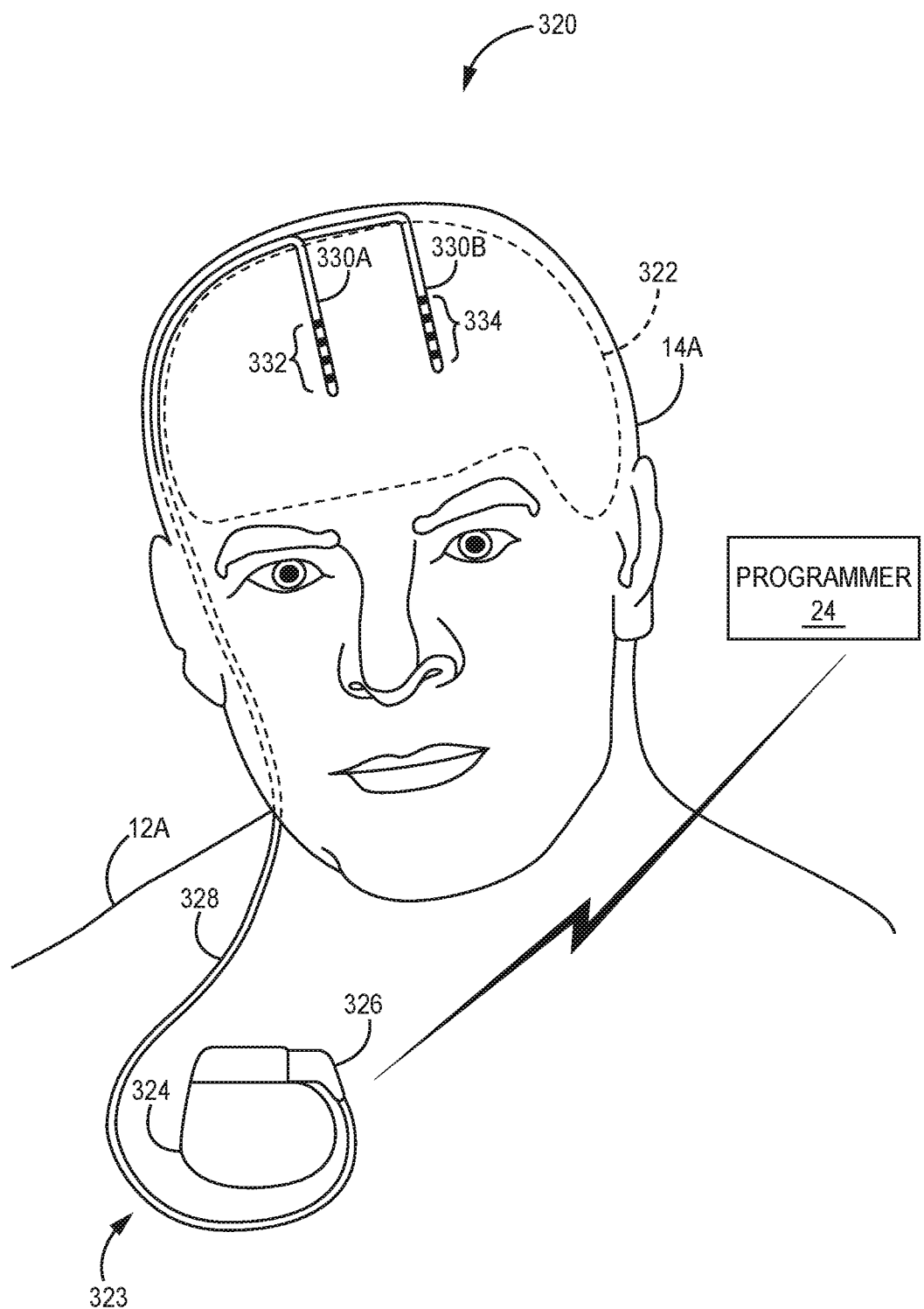
FIG. 1 is a conceptual diagram illustrating an example system that includes an implantable medical device (IMD) configured to deliver deep brain stimulation (DBS) to a patient.

This disclosure is generally directed to devices, systems, and techniques for enabling a clinician (e.g., doctor, nurse, or other healthcare professional) to specify or design a construction and/or configuration for a medical device, such as an implantable or external electrical stimulator. While it will be appreciated that the systems and techniques of this disclosure are equally applicable to implantable as well as external stimulators, various examples are described with respect to an implantable medical device (IMD). In some cases, the medical device may deliver a therapeutic agent to the patient instead of, or in addition to, electrical stimulation, and components attachable to the IMD may include, for example, catheters. In some cases, the medical device may deliver both electrical stimulation and a drug (or other therapeutic agent) via a combination lead catheter that carries one or more electrodes for delivery of stimulation, and includes one or more passages for delivery of a therapeutic agent. A combination of deep brain stimulation and drug delivery, for example, may be useful to treat certain neurological disorders.

Various aspects of this disclosure are directed to systems in which a clinician can build, configure, or reconfigure a representation of a stimulator using a graphical interface tool, e.g., provided by an IMD programming device. In various examples, this disclosure is directed to techniques for providing interactive UI-based tools that the clinician can utilize to specify the attachment of various devices, such as different types of electrical leads, adapters, catheters, or extensions to ports, connection points, or headers of the "can" of a stimulator representation. In some implementations, the interactive tool may run a "smart" algorithm, which may dynamically update options available to the clinician and/or provide suggestions to the clinician in configuring the stimulator representation. Additionally, the interactive tool may be configured to offer options of attachments (e.g., leads, adapters, and extensions), based on heuristic data available for specific implantation arrangements or stimulation configurations.

As used herein, a "port" may refer to an interface, such as a female connector, through which an attachment (e.g., a lead or a catheter) may be connected to the header, such as by "plugging in" the attachment via the port. Ports may include varying numbers of connection points, such as electrical connection points, through which the attachment can form a logical connection with a stimulation controller. In general, a port is a point of physical connection to the can or controller of the medical device, which may receive an attachable component, such as a lead. In some examples, ports may be formed in a header of the can or controller and/or may receive a proximal portion an attachable component, e.g., connector of a lead. A port may be point of electrical or fluid communication from inside the can or controller, which may be hermetically sealed, to the attachable component. The representation of a port in an interactive UI according to this disclosure may be a point of logical connection that indicates the actual or planned attachment of a component with a controller or can.

FIG. 1 is a conceptual diagram illustrating example system 320 that includes stimulation controller 324 configured to deliver deep brain stimulation (DBS) to patient 12A. Implantable medical device (IMD) 323 includes stimulation controller 324, connector 326, lead extension 328, and leads 330A and 330B. Although the particular example of FIG. 1 is described herein with respect to DBS, aspects of this disclosure may be applicable to other types of electrical stimulation, such as spinal cord stimulation, pelvic floor stimulation, gastric stimulation, cardiac stimulation, and various others. In the example of FIG. 1, for deep brain stimulation (DBS), system 320 may be configured to treat a patient condition, such as a movement disorder, neurodegenerative impairment, a mood disorder or a seizure disorder of patient 12A. Patient 12A ordinarily will be a human patient. In some cases, however, therapy system 320 may be applied to other mammalian or non-mammalian, non-human patients.

While movement disorders and neurodegenerative impairment are primarily referred to herein, in other examples, therapy system 320 may provide therapy to manage symptoms of other patient conditions, such as, but not limited to, seizure disorders (e.g., epilepsy) or mood (or psychological) disorders (e.g., major depressive disorder (MDD), bipolar disorder, anxiety disorders, post-traumatic stress disorder, dysthymic disorder, and obsessive-compulsive disorder (OCD)). At least some of these disorders may be manifested in one or more patient movement behaviors. As described herein, a movement disorder or other neurodegenerative impairment may include symptoms such as, for example, muscle control impairment, motion impairment or other movement problems, such as rigidity, spasticity, bradykinesia, rhythmic hyperkinesia, nonrhythmic hyperkinesia, and akinesia. In some cases, the movement disorder may be a symptom of Parkinson's disease. However, the movement disorder may be attributable to other patient conditions.

Example therapy system 320 includes medical device programmer 24, stimulation controller 324, lead extension 328, and leads 330A and 330B with respective sets of electrodes 332, 334. As described above, stimulation controller 324, connector 326, lead extension 328, and leads 330A and 330B form IMD 323. In the example shown in FIG. 1, electrodes 332, 334 of leads 330A, 330B are positioned to deliver electrical stimulation to a tissue site within brain 322, such as a deep brain site under the dura mater of brain 322 of patient 12A. In some examples, delivery of stimulation to one or more regions of brain 322, such as the subthalamic nucleus, globus pallidus or thalamus, may be an effective treatment to manage movement disorders, such as Parkinson's disease. Electrodes 332, 334 are also positioned to sense bioelectrical brain signals within brain 322 of patient 12A. In some examples, some of electrodes 332, 334 may be configured to sense bioelectrical brain signals and others of electrodes 332, 334 may be configured to deliver electrical stimulation to brain 322. In other examples, all of electrodes 332, 334 are configured to both sense bioelectrical brain signals and deliver electrical stimulation to brain 322.

Stimulation controller 324 includes a therapy module that includes a stimulation generator that generates and delivers electrical stimulation therapy to patient 12A via a subset of electrodes 332, 334 of leads 330A and 330B, respectively. The subset of electrodes 332, 334 that are used to deliver electrical stimulation to patient 12A, and, in some cases, the polarity of the subset of electrodes 332, 334, may be referred to as a stimulation electrode combination or configuration. As described in further detail below, the stimulation electrode combination can be selected for a particular patient 12A and target tissue site (e.g., selected based on the patient condition) based on one or more frequency domain characteristics of a bioelectrical brain signal (e.g., a patient parameter) that is sensed by one or more groups of electrodes 332, 334 that are associated with the stimulation electrode combination. The group of electrodes 332, 334 includes at least two electrodes and can include a plurality of electrodes.

In some examples, bioelectrical signals sensed within brain 322 may reflect changes in electrical current produced by the sum of electrical potential differences across brain tissue. Examples of bioelectrical brain signals include, but are not limited to, electrical signals generated from local field potentials (LFP) sensed within one or more regions of brain 322, such as an electroencephalogram (EEG) signal, or an electrocorticogram (ECoG) signal. Local field potentials, however, may include a broader genus of electrical signals within brain 322 of patient 12A. Each of these signals may be correlated or calibrated with the identified patient behavior and used for feedback in controlling the delivery of therapy.

In some examples, the bioelectrical brain signals that are used to select a stimulation electrode combination may be sensed within the same region of brain 322 as the target tissue site for the electrical stimulation. As previously indicated, these tissue sites may include tissue sites within the thalamus, subthalamic nucleus or globus pallidus of brain 322, as well as other target tissue sites. The specific target tissue sites and/or regions within brain 322 may be selected based on the patient condition. Thus, in some examples, both a stimulation electrode combination and sense electrode combinations may be selected from the same set of electrodes 332, 334. In other examples, the electrodes used for delivering electrical stimulation may be different than the electrodes used for sensing bioelectrical brain signals.

Electrical stimulation generated by stimulation controller 324 may be configured to manage a variety of disorders and conditions. In some examples, the stimulation generator of stimulation controller 324 is configured to generate and deliver electrical pulses to patient 12A via electrodes of a selected stimulation electrode combination. However, in other examples, the stimulation generator of stimulation controller 324 may be configured to generate and deliver a continuous wave signal, e.g., a sine wave or triangle wave. In either case, a signal generator within stimulation controller 324 may generate the electrical stimulation therapy for DBS according to a therapy program that is selected at that given time in therapy. In examples in which stimulation controller 324 delivers electrical stimulation in the form of stimulation pulses, a therapy program may include a set of therapy parameter values, such as a stimulation electrode combination for delivering stimulation to patient 12A, pulse frequency, pulse width, and a current or voltage amplitude of the pulses. As previously indicated, the stimulation electrode combination may indicate the specific electrodes 332, 334 that are selected to deliver stimulation signals to tissue of patient 12A and the respective polarity of the selected electrodes.

Stimulation controller 324 may be implanted within a subcutaneous pocket above the clavicle, or, alternatively, the abdomen, back or buttocks of patient 12A, on or within cranium 14A or at any other suitable site within patient 12A. Generally, stimulation controller 324 is constructed of a biocompatible material that resists corrosion and degradation from bodily fluids. Stimulation controller 324 may comprise a hermetic housing to substantially enclose components, such as a processor, therapy module, and memory.

As shown in FIG. 1, implanted lead extension 328 is coupled to stimulation controller 324 via connector 30 (also referred to as a connector block or a header of stimulation controller 324). In the example of FIG. 1, lead extension 328 traverses from the implant site of stimulation controller 324 and along the neck of patient 12A to cranium 14A of patient 12A to access brain 322. In the example shown in FIG. 1, leads 330A and 330B (collectively "leads 330") are implanted within the right and left hemispheres, respectively, of patient 12A in order deliver electrical stimulation to one or more regions of brain 322, which may be selected based on the patient condition or disorder controlled by therapy system 320. The specific target tissue site and the stimulation electrodes used to deliver stimulation to the target tissue site, however, may be selected, e.g., according to the identified patient behaviors and/or other sensed patient parameters. Other implant sites for leads 330 and/or stimulation controller 324 are contemplated. For example, stimulation controller 324 may be implanted on or within cranium 14A, in some examples. Or, leads 330 may be implanted within the same hemisphere or stimulation controller 324 may be coupled to a single lead.

Although leads 330 are shown in FIG. 1 as being coupled to a common lead extension 328, in other examples, leads 330 may be coupled to stimulation controller 324 via separate lead extensions or directly to connector 326. Leads 330 may be positioned to deliver electrical stimulation to one or more target tissue sites within brain 322 to manage patient symptoms associated with a movement disorder of patient 12A. Leads 330 may be implanted to position electrodes 332, 334 at desired locations of brain 322 through respective holes in cranium 14A. Leads 330 may be placed at any location within brain 322 such that electrodes 332, 334 are capable of providing electrical stimulation to target tissue sites within brain 322 during treatment. For example, electrodes 332, 334 may be surgically implanted under the dura mater of brain 322 or within the cerebral cortex of brain 322 via a burr hole in cranium 14A of patient 12A, and electrically coupled to stimulation controller 324 via one or more leads 330.

Example techniques for delivering therapy to manage a movement disorder are described in U.S. Pat. No. 8,121,694, to Molnar et al., entitled, "THERAPY CONTROL BASED ON A PATIENT MOVEMENT STATE," which was issued on Feb. 21, 2012, and which is incorporated herein by reference in its entirety. In some examples described by U.S. Pat. No. 8,121,694 to Molnar et al., a brain signal, such as an EEG or ECoG signal, may be used to determine whether a patient is in a movement state or a rest state. The movement state includes the state in which the patient is generating thoughts of movement (i.e., is intending to move), attempting to initiate movement or is actually undergoing movement. The movement state or rest state determination may then be used to control therapy delivery. For example, upon detecting a movement state of the patient, therapy delivery may be activated in order to help patient 12A initiate movement or maintain movement, and upon detecting a rest state of patient 12A, therapy delivery may be deactivated or otherwise modified.

In the example shown in FIG. 1, electrodes 332, 334 of leads 330 are shown as ring electrodes. Ring electrodes may be used in DBS applications because they are relatively simple to program and are capable of delivering an electrical field to any tissue adjacent to electrodes 332, 334. In other examples, electrodes 332, 334 may have different configurations. For example, in some examples, at least some of the electrodes 332, 334 of leads 330 may have a complex electrode array geometry, e.g., with segmented electrodes and/or pad electrodes, that are capable of producing shaped electrical fields. The complex electrode array geometry may include multiple electrodes (e.g., partial ring or segmented electrodes) around the outer perimeter of each lead 330, rather than one ring electrode. In this manner, electrical stimulation may be directed in a specific direction from leads 330 to enhance therapy efficacy and reduce possible adverse side effects from stimulating a large volume of tissue. In some examples, a housing of stimulation controller 324 may include one or more stimulation and/or sensing electrodes. In alternative examples, leads 330 may have shapes other than elongated cylinders as shown in FIG. 1. For example, leads 330 may be paddle leads, spherical leads, segmented electrode leads, pad electrode leads, bendable leads, or any other type of shape effective in treating patient 12A and/or minimizing invasiveness of leads 330. Leads 330 may include leads with different numbers and/or types of electrodes. For instance, one or more leads 330 may include ring electrodes, segmented electrodes, or pad electrodes. Additionally, leads 330 may include one or both of cylindrical leads, or paddle-shaped leads. A paddle-shaped lead may include a distal portion that is flat and relatively broad, thereby giving the entire lead a paddle-like shape. Paddle-shaped leads may include pad electrodes, arranged in an array (e.g., one-dimensional, two-dimensional, and so on) across the distal portion of the paddle-shaped lead. Cylindrical leads may include segmented electrodes arranged in an array (e.g., one-dimensional, two-dimensional, and so on) around the body of the cylindrical lead. In some examples, the segmented electrodes may be positioned on the distal end of the cylindrical lead.

In the example shown in FIG. 1, stimulation controller 324 includes a memory (shown in FIG. 3) to store a plurality of therapy programs that each define a set of therapy parameter values. In some examples, stimulation controller 324 may select a therapy program from the memory based on various parameters, such as sensed patient parameters and the identified patient behaviors. Stimulation controller 324 may generate electrical stimulation based on the selected therapy program to manage the patient symptoms associated with a movement disorder.

External programmer 24 wirelessly communicates with stimulation controller 324 as needed to provide or retrieve therapy information. Programmer 24 is an external computing device (e.g., computing device 54 of FIG. 3) that the user, e.g., clinician 22 and/or patient 12A, may use to communicate with stimulation controller 324. For example, programmer 24 may be a clinician programmer that the clinician uses to communicate with stimulation controller 324 and program one or more therapy programs for stimulation controller 324.

When programmer 24 is configured for use by the clinician, programmer 24 may be used to transmit initial programming information to stimulation controller 324. This initial information may include hardware information, such as the type of leads 330 and the electrode arrangement, the position of leads 330 within brain 322, the configuration of electrode array 332, 334, initial programs defining therapy parameter values, and any other information the clinician desires to program into stimulation controller 324. Programmer 24 may also be capable of completing functional tests (e.g., measuring the impedance of electrodes 332, 334 of leads 330).

The clinician may also store therapy programs within stimulation controller 324 with the aid of programmer 24. During a programming session, the clinician may determine one or more therapy programs that may provide efficacious therapy to patient 12A to address symptoms associated with the patient condition, and, in some cases, specific to one or more different patient states, such as a sleep state, movement state or rest state. For example, the clinician may select one or more stimulation electrode combinations with which stimulation is delivered to brain 322.

Therapy system 320 may be implemented to provide chronic stimulation therapy to patient 12A over the course of several months or years. In other examples, however, system 320 may also be employed on a trial basis to evaluate therapy before committing to full implantation. If implemented temporarily, some components of system 320 may not be implanted within patient 12A. For example, patient 12A may be fitted with an external medical device, such as a trial stimulator, rather than stimulation controller 324. The external medical device may be coupled to percutaneous leads or to implanted leads via a percutaneous extension. If the delivery of stimulation using the trial stimulator indicates that DBS system 320 would provide effective treatment to patient 12A, the clinician may implant a chronic stimulator within patient 12A for relatively long-term treatment.

Stimulation controller 324 may determine a therapy to be delivered based on selection of one or more therapy parameter values (e.g., a set of therapy parameters or a therapy program) that at least partially define the therapy. In other examples, other computing devices may be configured to determine the therapy based on the identified patient behavior (e.g., movement disorder). For example, a networked server, programmer 24, or any other computing device may determine the therapy.

Although stimulation controller 324 is described as delivering electrical stimulation therapy to brain 322, stimulation controller 324 may be configured to direct electrical stimulation to other anatomical regions of patient 12A. In other examples, as described with respect to FIG. 2, an IMD may provide other electrical stimulation such as spinal cord stimulation to treat chronic pain.

Figure 2:
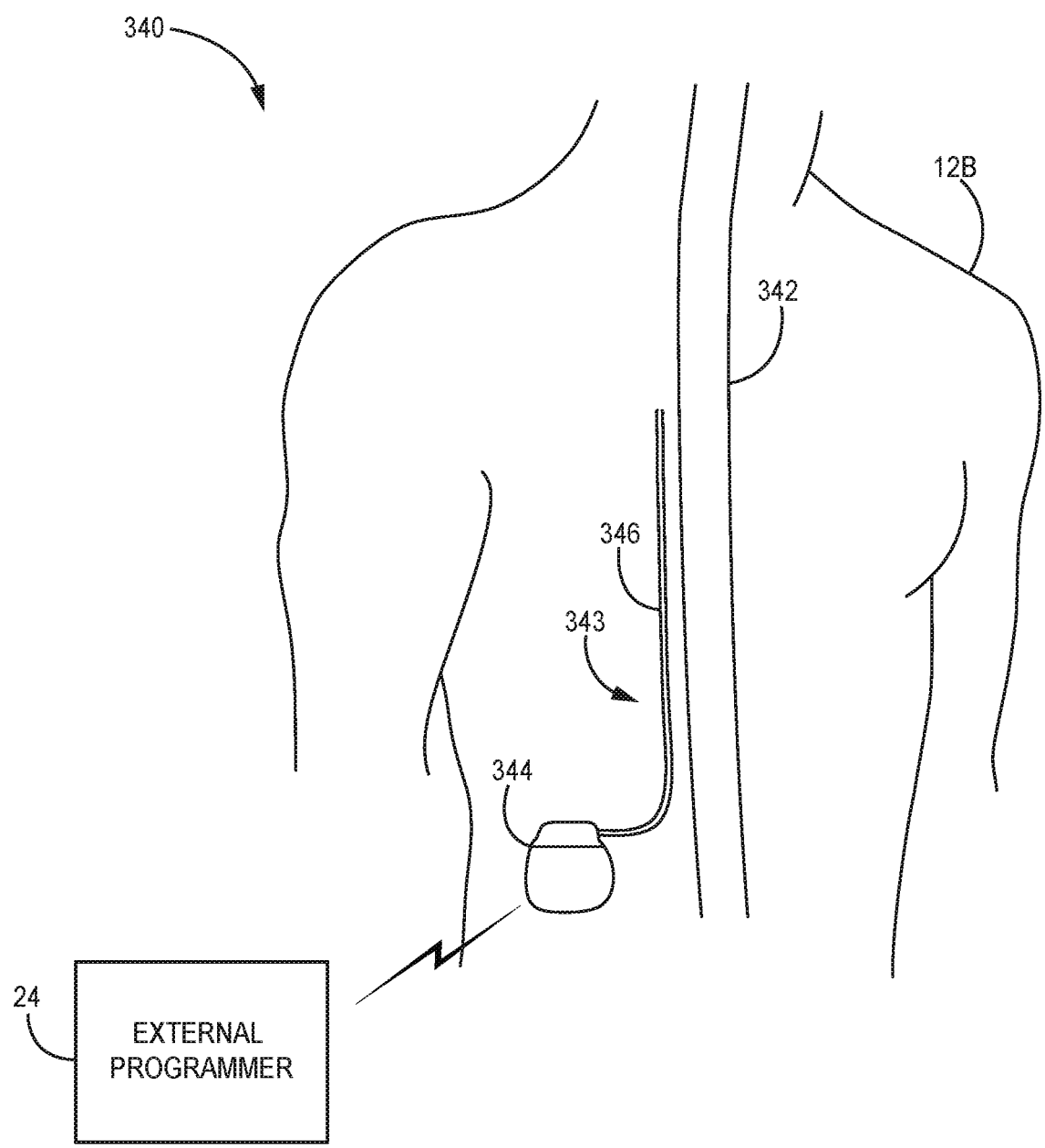
FIG. 2 is a conceptual diagram illustrating an example system that includes an IMD configured to deliver spinal cord stimulation (SCS) to a patient.

FIG. 2 is a conceptual diagram illustrating example system 340 that includes stimulation controller 344 configured to deliver spinal cord stimulation (SCS) to a patient 12B. Although the particular example of FIG. 2 is described herein with respect to SCS, aspects of this disclosure may be applicable with respect to other types of electrical stimulation, such as pelvic floor stimulation, gastric stimulation, peripheral nerve stimulation and various other types of nerve or muscular stimulation.

As shown in FIG. 2, system 340 includes stimulation controller 344 and external programmer 24. Stimulation controller 344 and lead 346 collectively form IMD 343. Generally, stimulation controller 344 may be a chronic electrical stimulator that remains implanted within patient 12B for weeks, months, or even years. Stimulation controller 344 may be similar to stimulation controller 324 of FIG. 1. In the example of FIG. 2, stimulation controller 344 and lead 346 may be directed to delivering SCS therapy. In other examples, stimulation controller 344 may be a temporary, or trial, stimulator used to screen or evaluate the efficacy of electrical stimulation for chronic therapy. Stimulation controller 344 may be implanted in a subcutaneous tissue pocket, within one or more layers of muscle, or other internal location. Stimulation controller 344 may be coupled to one or more leads 346.

Electrical stimulation energy, which may be constant current or constant voltage based pulses, for example, is delivered from stimulation controller 344 to one or more targeted locations within patient 12B via one or more electrodes (not shown) of lead 346. The parameters for a program that controls delivery of stimulation energy by stimulation controller 344 may include information identifying which electrodes have been selected for delivery of stimulation according to a stimulation program, the combination of the selected electrodes, and the polarities of the selected electrodes, i.e., the electrode configuration for the program, and voltage or current amplitude, pulse frequency (or pulse rate), pulse shape, and pulse width of stimulation delivered by the electrodes. Electrical stimulation may be delivered in the form of stimulation pulses or continuous waveforms, for example. In various examples, options for the combination of electrodes, the polarities of the selected electrodes, and the parameters of the stimulation delivered by the selected electrodes may be limited, such as may be represented in a finite list. In some examples, the options may be selected automatically, based on which of the various leads is/are connected to stimulation controller 344.

In the example of FIG. 2, lead 346 is disposed within patient 12B, e.g., implanted within patient 12B. Lead 346 may be tunneled through tissue of patient 12B from along spinal cord 342 to a subcutaneous tissue pocket or other internal location where stimulation controller 344 is disposed. Although lead 346 may be a single lead, lead 346 may include a lead extension or other segments that may aid in implantation or positioning of lead 346. In addition, a proximal end of lead 346 may include a connector (not shown) that electrically couples to a header of stimulation controller 344. Although only one lead 346 is shown in FIG. 2, system 340 may include two or more leads, each coupled to stimulation controller 344 and directed to similar or different target tissue sites. For example, multiple leads may be disposed along spinal cord 342 or leads may be directed to spinal cord 342 and/or other locations within patient 12B.

Lead 346 may carry one or more electrodes that are placed adjacent to the target tissue, e.g., spinal cord 342 for spinal cord stimulation (SCS) therapy. One or more electrodes may be disposed at or near a distal tip of lead 346 and/or at other positions at intermediate points along lead 346, for example. Electrodes of lead 346 transfer electrical stimulation generated by an electrical stimulation generator in stimulation controller 344 to tissue of patient 12B. The electrodes may be electrode pads on a paddle lead, circular (e.g., ring) electrodes surrounding the body of the lead, conformable electrodes, cuff electrodes, segmented electrodes (e.g., electrodes disposed at different circumferential positions around the lead instead of a continuous ring electrode), or any other type of electrodes capable of forming unipolar, bipolar or multipolar electrode combinations for therapy. In general, ring electrodes arranged at different axial positions at the distal ends of lead 346 will be described for purposes of illustration.

Similar to stimulation controller 324 of FIG. 1, stimulation controller 344 of FIG. 2 delivers electrical stimulation therapy to patient 12B via selected combinations of electrodes carried by lead 346. The target tissue for the electrical stimulation therapy may be any tissue affected by electrical stimulation energy, which may be in the form of electrical stimulation pulses or waveforms. In some examples, the target tissue includes nerves, smooth muscle, and skeletal muscle. In the example illustrated by FIG. 2, the target tissue for electrical stimulation delivered via lead 346 is tissue proximate spinal cord 342 (e.g., one or more target locations of the dorsal columns or one or more dorsal roots that branch from spinal cord 342). Lead 346 may be introduced into spinal cord 342 via any suitable region, such as the thoracic, cervical or lumbar regions. Stimulation of dorsal columns, dorsal roots, and/or peripheral nerves (e.g., afferent nerves) may, for example, prevent pain signals from traveling through spinal cord 342 and to the brain of the patient. Patient 12B may perceive the interruption of pain signals as a reduction in pain and, therefore, efficacious therapy results. For treatment of other disorders, lead 346 may be introduced at any exterior location of patient 12B.

Although lead 346 is described as generally delivering or transmitting electrical stimulation signals, lead 346 may additionally transmit electrical signals obtained via electrodes or various sensors carried by the lead from patient 12B to stimulation controller 344 for monitoring. For example, stimulation controller 344 may utilize detected nerve impulses or muscle impulses to diagnose the condition of patient 12B or adjust the delivered stimulation therapy. Lead 346 may thus transmit electrical signals to and from patient 12B.

A user, such as a clinician or patient 12B, may interact with a user interface of an external programmer 24 to program stimulation controller 344. Programming of stimulation controller 344 may refer generally to the generation and transfer of commands, programs, or other information to control the operation of stimulation controller 344. In this manner, stimulation controller 344 may receive the transferred commands and programs from programmer 24 to control stimulation therapy. For example, external programmer 24 may transmit programs, parameter adjustments, program selections, group selections, user input, or other information to control the operation of stimulation controller 344, e.g., by wireless telemetry or wired connection.

Stimulation controller 324 or 344 and programmer 24 may communicate via wireless communication using any techniques known in the art. Examples of communication techniques may include, for example, radiofrequency (RF) telemetry and inductive coupling, but other techniques are also contemplated. In some examples, programmer 24 may include a communication head that may be placed proximate to the patient's body near the stimulation controller 324 or 344 implant site in order to improve the quality or security of communication between stimulation controller 324 or 344 and programmer 24. Communication between programmer 24 and stimulation controller 324 or 344 may occur during power transmission or separate from power transmission.

Although stimulation controller 324 and 344 are generally described as being implantable in FIGS. 1 and 2, techniques of this disclosure may also be applicable to external or partially external medical device in other examples. For example, stimulation controller 324 or 344 may instead be configured as an external medical device coupled to one or more percutaneous medical leads. The external medical device may be a chronic, temporary, or trial electrical stimulator. In addition, an external electrical stimulator may be used in addition to one or more IMDs 340 or 344 to deliver electrical stimulation.

Figure 3:
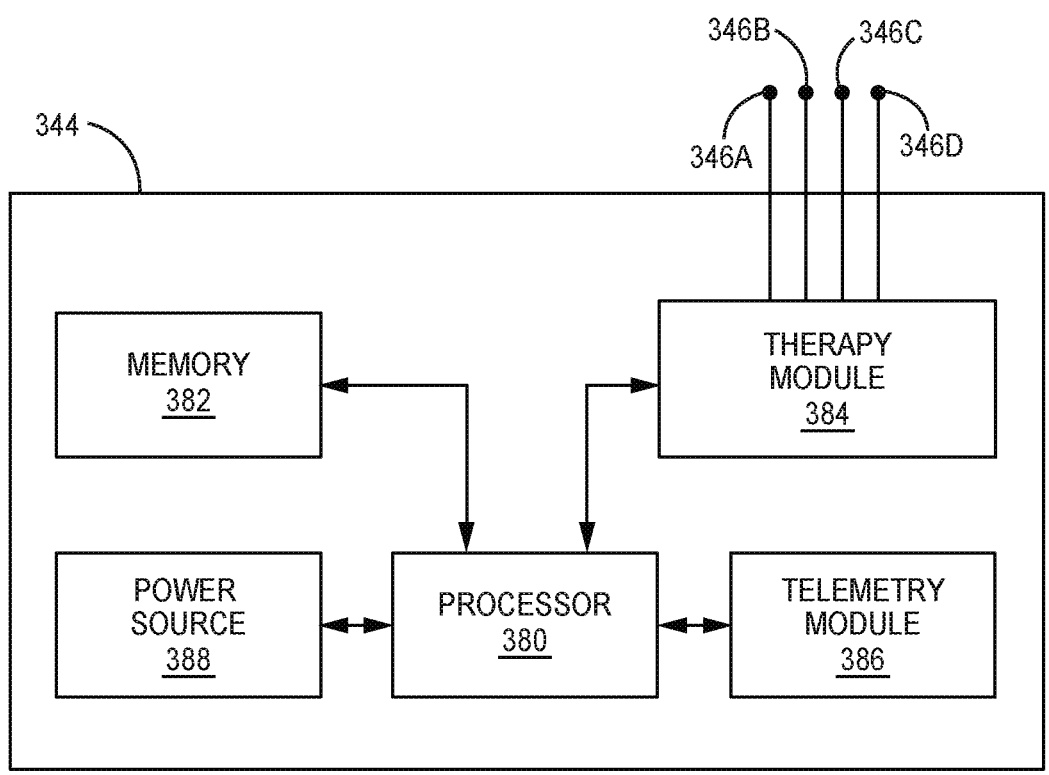
FIG. 3 is a block diagram of the example IMD of FIG. 2 for delivering spinal cord stimulation (SCS) therapy.

FIG. 3 is a block diagram illustrating example components of stimulation controller 344 of FIG. 2 for delivering spinal cord stimulation (SCS) therapy. The same or similar components may be provided for stimulation controller 324 for delivering DBS therapy, or to other IMDs for delivering other electrical stimulation therapies to patient tissue. As shown in the example of FIG. 3, stimulation controller 344 includes processor 380, therapy module 384, power source 388, memory 382, and telemetry module 386. In other examples, stimulation controller 344 may include a greater or fewer number of components. For example, stimulation controller 344 may also include one or more sensors.

In general, stimulation controller 344 may comprise any suitable arrangement of hardware, alone or in combination with software and/or firmware, to perform the various techniques described herein attributed to stimulation controller 344 and processor 380. In various examples, stimulation controller 344 may include one or more processors 30, such as one or more microprocessors, digital signal processors (DSPs), application specific integrated circuits (ASICs), field programmable gate arrays (FPGAs), or any other equivalent integrated or discrete logic circuitry, as well as any combinations of such components. stimulation controller 344 also, in various examples, may include a memory 382, such as random access memory (RAM), read only memory (ROM), programmable read only memory (PROM), erasable programmable read only memory (EPROM), electronically erasable programmable read only memory (EEPROM), flash memory, comprising executable instructions for causing the one or more processors to perform the actions attributed to them. Moreover, although processor 380, therapy module 384, and telemetry module 386 are described as separate modules, in some examples, processor 380, therapy module 384, and telemetry module 386 may be functionally integrated. In some examples, processor 380, therapy module 384, and telemetry module 386 may correspond to individual hardware units, such as ASICs, DSPs, FPGAs, or other hardware units.

Memory 382 (e.g., a storage device) may store therapy programs or other instructions that specify therapy parameter values for the therapy provided by therapy module 384 and stimulation controller 344. In some examples, memory 382 may also store instructions for communication between stimulation controller 344 and programmer 24, or any other instructions required to perform tasks attributed to stimulation controller 344. Memory 382 may also store feedback control instructions similar to feedback control 364 of stimulation controller 324.

Generally, therapy module 384 may generate and deliver electrical stimulation under the control of processor 380. In some examples, processor 380 controls therapy module 384 by accessing memory 382 to selectively access and load at least one of the stimulation programs to therapy module 384. For example, in operation, processor 380 may access memory 382 to load one of the stimulation programs to therapy module 384. In such examples, relevant stimulation parameters may include a voltage amplitude, a current amplitude, a pulse frequency, a pulse width, a duty cycle, one or more spatial electrode movement patterns that define the combination of electrodes 346A, 346B, 346C, and 346D that therapy module 384 uses to deliver the electrical stimulation signal.

Therapy module 384, under the control of processor 380, generates stimulation signals for delivery to patient 12B via electrodes carried on one or more leads 346. An example range of electrical stimulation parameters that may be effective to provide therapy to a patient may include:

1. Frequency: between approximately 0.5 Hz and approximately 10000 Hz, more preferably between 5 Hz and 250 Hz, and more preferably between 30 Hz and 130 Hz.

2. Voltage Amplitude: between approximately 0.1 volts and approximately 50 volts, such as between approximately 0.5 volts and approximately 20 volts, or approximately 5 volts.

3. Current Amplitude: A current amplitude may be defined as the biological load in which the voltage is delivered. In a current-controlled system, the current amplitude, assuming a lower level impedance of approximately 500 ohms, may be between approximately 0.2 milliAmps to approximately 100 milliAmps, such as between approximately 1 milliAmps and approximately 40 milliAmps, or approximately 10 milliAmps. However, in some examples, the impedance may range between about 200 ohms and about 2 kiloohms.

4. Pulse Width: between approximately 10 microseconds and approximately 5000 microseconds, such as between approximately 100 microseconds and approximately 1000 microseconds, or between approximately 180 microseconds and approximately 450 microseconds.

Processor 380 may also control the exchange of information with programmer 24 using telemetry module 386. Telemetry module 386 may be configured for wireless communication using radio frequency protocols or inductive communication protocols. Telemetry module 386 may include one or more antennas configured to communicate with programmer 24, for example. Processor 380 may transmit operational information and receive therapy programs or therapy parameter adjustments via telemetry module 386.

Figure 4:
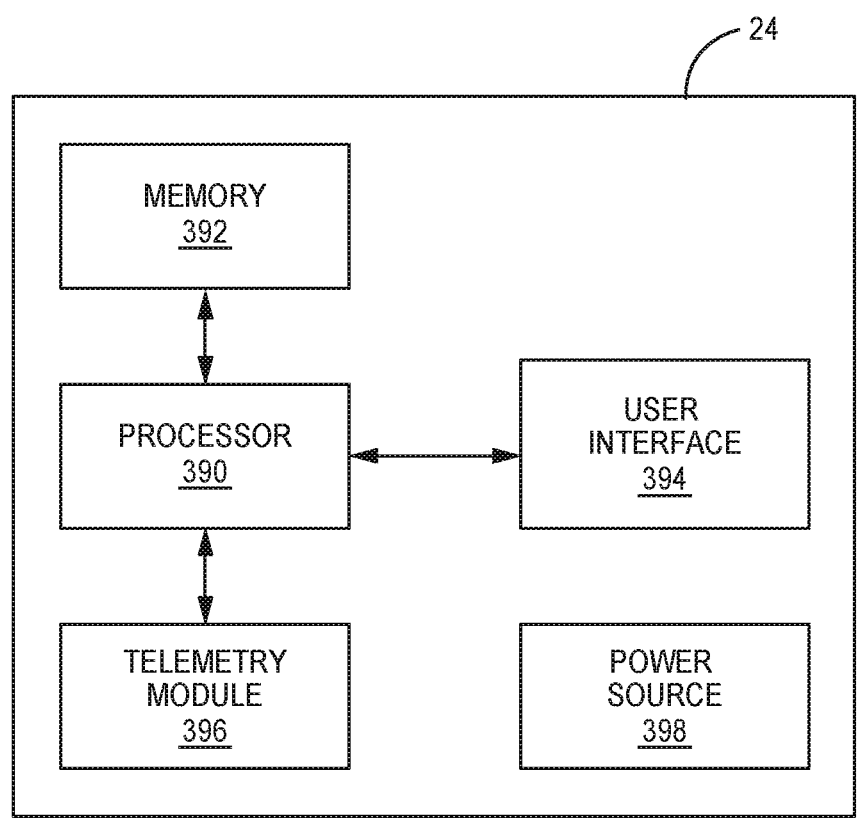
FIG. 4 is a block diagram of the external programmer of FIGS. 1 and 2.

FIG. 4 is a block diagram of external programmer 24 of FIGS. 1 and 2. Although programmer 24 may generally be described as a hand-held device, programmer 24 may be a larger portable device or a more stationary device. In addition, in other examples, programmer 24 may be included as part of an external charging device or include the functionality of an external charging device. As illustrated in FIG. 4, programmer 24 may include a processor 390, memory 392, user interface 394, telemetry module 396, and power source 398. Memory 392 may store instructions that, when executed by processor 390, cause processor 390 and external programmer 24 to provide the functionality ascribed to external programmer 24 throughout this disclosure.

In general, programmer 24 comprises any suitable arrangement of hardware, alone or in combination with software and/or firmware, to perform the techniques attributed to programmer 24, and processor 390, user interface 394, and telemetry module 396 of programmer 24. In various examples, programmer 24 may include one or more processors, such as one or more microprocessors, DSPs, ASICs, FPGAs, or any other equivalent integrated or discrete logic circuitry, as well as any combinations of such components. Programmer 24 also, in various examples, may include a memory 392, such as RAM, ROM, PROM, EPROM, EEPROM, flash memory, a hard disk, a CD-ROM, comprising executable instructions for causing the one or more processors to perform the actions attributed to them. Moreover, although processor 390 and telemetry module 396 are described as separate modules, in some examples, processor 390 and telemetry module 396 are functionally integrated. In some examples, processor 390 and telemetry module 396 correspond to individual hardware units, such as ASICs, DSPs, FPGAs, or other hardware units.

User interface 394 may include a button or keypad, lights, a speaker for voice commands, a display, such as a liquid crystal (LCD), light-emitting diode (LED), or organic light-emitting diode (OLED). In some examples the display may be a touch screen. User interface 394 may be configured to display any information related to the delivery of stimulation therapy, sensed patient parameter values, or any other such information. User interface 394 may also receive user input. The input may be, for example, in the form of pressing a button on a keypad or selecting or manipulating an icon, e.g., with a pointing device or from a touch screen. The input may request starting or stopping electrical stimulation, or the input may request some other change to the delivery of electrical stimulation, e.g., such as a change in current or voltage amplitude, a change in pulse rate, and/or a change in pulse width.

Telemetry module 396 may support wireless communication between stimulation controller 324 and programmer 24 under the control of processor 390. Telemetry module 396 may also be configured to communicate with another computing device via wireless communication techniques, or direct communication through a wired connection. In some examples, telemetry module 396 may be substantially similar to telemetry module 386 of stimulation controller 324 described herein, providing wireless communication via an RF or proximal inductive medium. In some examples, telemetry module 396 may include an antenna, which may take on a variety of forms, such as an internal or external antenna.

Examples of local wireless communication techniques that may be employed to facilitate communication between programmer 24 and stimulation controller 324 include RF communication according to the 802.11 or Bluetooth specification sets or other standard or proprietary telemetry protocols. In this manner, other external devices may be capable of communicating with programmer 24 without needing to establish a secure wireless connection.

In some examples, selection of therapy parameters or therapy programs may be transmitted to a medical device (e.g., stimulation controller 324 or stimulation controller 344) for delivery to patient 12. According to aspects of this disclosure, memory 392 may store or include a plurality of programs, where each program includes a parameter set that defines stimulation therapy. Additionally, according to aspects of this disclosure, memory 392 may store device configurations (or configurations for representations of medical devices) that can be used at the discretion of a clinician. For instance, the clinician may configure representations of a medical device, to form multiple configurations. In turn, the clinician may store one or more of the configurations to memory 392. The clinician, and/or subsequent users of programmer 24 may, at their discretion, propagate one or more of the stored configurations to actual medical devices for use in patients.

FIGS. 5-11 are screenshots of example UIs illustrating the use of interactive tools of this disclosure to design and/or specify a construction and configuration for an implantable stimulator with a total of sixteen (16) electrodes. The interactive tools of this disclosure may implement the illustrated UIs on a programmer, such as programmer 24 of FIGS. 1-4. As shown in FIGS. 5-11, each of the respective UIs may include three sections or panels, namely a connection map, a workspace, and an option tray.

While illustrated and discussed with respect to electrical stimulators for purposes of example, the techniques and systems of this disclosure may also be applied for configuring one or more medical devices that deliver therapeutic agent(s), or some combination of both electrical stimulation and therapeutic agent(s) to the system. As such, it will be appreciated that the systems and techniques of this disclosure may be applied to a device that delivers a therapeutic agent to the body, such as a drug pump with one or more catheters attached. Additionally, the systems and techniques of this disclosure may deliver the combination of therapeutic agent(s) and electrical stimulation via a catheter that carries electrodes. As an example, the combination of electrical stimulation and therapeutic agent(s) may apply to various types of therapy, such as DBS.

Figure 5:
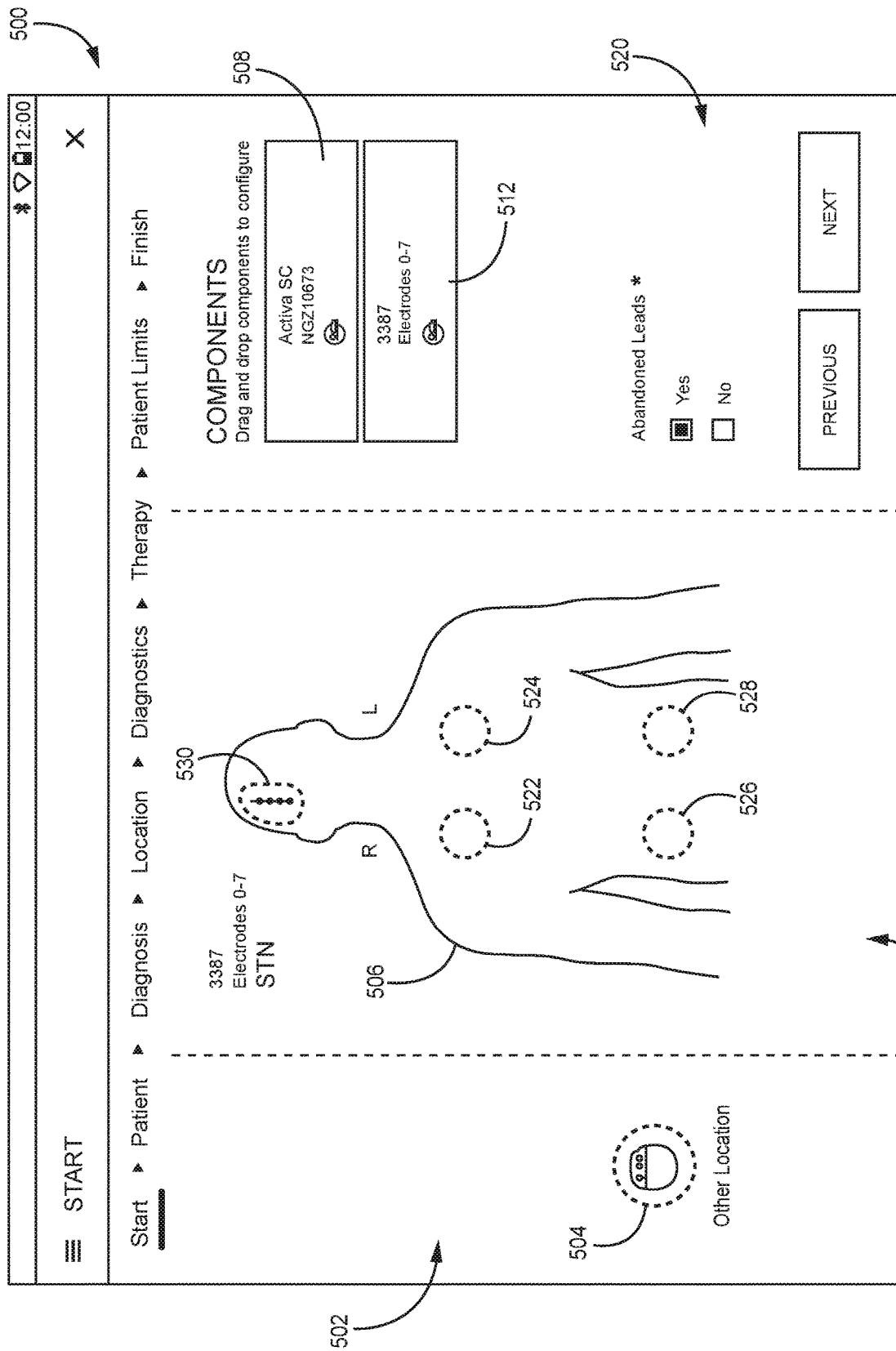
FIGS. 5-11 are screenshots of example UIs illustrating the use of interactive tools of this disclosure to design and/or specify a construction and configuration for an implantable stimulator with a total of sixteen (16) electrodes.

In the case of UI 500 of FIG. 5, connection map 502 provides the clinician with drag-and-drop, click-and-drop, or otherwise movable or positionable representations of devices (e.g., an IMD or ENS) and/or representations of individual components (e.g., leads, extensions, catheters, etc.) that are attachable to the devices and that can be placed at various locations in/or on a representation of a patient's body. Workspace 510 provides the clinician with a schematic representation 506 of a patient's body. The clinician may use schematic 506 to select a location at which to drag and drop or otherwise position an instance of a stimulator controller, such as the one represented by component 508. In the case of UI 500, an instance of the stimulator controller may be positioned in a pectoral region of schematic 506, as an example. In examples in which the stimulation controller is used to deliver DBS, via one or more leads, representations of the leads may be in the cranial region of schematic 506.

Option tray 520 of UI 500A lists a representation of a selected component 508. The selected component 508, in the particular example of FIG. 5, is an implantable device, such as a stimulation controller, that has been selected for implantation in the patient. Option tray 520 also includes a representation of a selected component 512, which may have been previously selected for attachment to the stimulation controller, e.g., using the interfaces illustrated with respect to FIGS. 6-11. Both option tray 520 and workspace 510 indicate that attached lead representation 512 is currently specified as being connected to contacts 0-7 of stimulator representation 504. For instance, attached lead 512 may be connected to all eight contacts of a single port of stimulator 504, via eight corresponding contacts of attached lead 512.

A clinician may use UI 500 of FIG. 5 is used to build configuration information for an IMD, such as location data for the IMD in the body of the patient. An IMD, programmer, or other system component, e.g., a remote server, may be configured to record the location of implant of the IMD and the components with which the IMD is interconnected as specified using UI 500. Thus, the IMD or other component can report the location information for various purposes, such as prior to medical imaging (e.g., MRI), for determining compatibility of the components with imaging, restrictions on which portions of a patient may be imaged, or so that items appearing in images may be understood to be components of a medical device.

The clinician may select one of the components (e.g., 508 or 512), in option tray 520, such as by performing a "click" of the respective component 508 or 512, or by initiating a drag operation for the respective component 508 or 512. Upon selecting the appropriate component, processor 390 of programmer 24 may display one or more "anatomical dropzones" that represent locations in/on the patient's body where the selected component can be dropped. As an example, if the clinician selects component 508 from option tray 520, then processor 390 may display four anatomical dropzones (labeled 522-528) shown on the representation of the patient's body. In the illustrated example, anatomical dropzones 522-528 are positioned in the right pectoral region, left pectoral region, right abdomen area, and left abdomen area of the patient's body. In FIG. 5, anatomical dropzones 522-528 are shown using dashed-line bordered circles. In this manner, programmer 244 implements the techniques of this disclosure to provide guidance (using anatomical dropzones 522-528) to the clinician on the location(s) at which component 508 can be placed (e.g., implanted).

In the example of FIG. 5, connection map 502 also provides a fifth dropzone via alternate location indicator 504. Alternate location indicator 504 is labeled as "other" to indicate that a corresponding location is not shown in workspace 520. Instead, location indicator 504 may provide dropzone guidance with respect to another portion of the patient's anatomy, such as the buttocks. Alternate location indicator 504 is also illustrated in a similar fashion to anatomical dropzones 522-528, which in this particular example, is a circle with a dashed-line border. In some examples, the clinician may enter descriptive information about the implant location corresponding to alternate location indicator 504. As examples, processor 390 may provide a free-form text window or other text-entry element when alternate location indicator 504 is selected, or by presenting a dropdown menu. It will be appreciated that the text-entry and dropdown menu implementations of providing alternate location indicator 504 are not shown in FIG. 5 purely for ease of illustration purposes.

In a similar manner, if the clinician selects a lead (in this example, the lead labeled '3387') using component 512 of option tray 520, then processor 390 may display anatomical dropzone 530 for the lead. In one example, processor 390 may display two anatomical dropzones, one shown on each side of the patient's head, for stimulating the right and left hemispheres of the brain, respectively. For ease of illustration purposes only, FIG. 5 includes only a single anatomical dropzone (anatomical dropzone 530) in the patient's head, via schematic 506. Each anatomical dropzone in this example may accommodate two or more leads, because two or more leads can be placed in a single hemisphere of the brain for DBS. Processor 390 may update the representation of the anatomical dropzones for the leads once a single lead is placed in the dropzone. However, an anatomical dropzone with one lead may still remain "available" for placement of the second lead, in some examples, thereby providing the clinician with guidance for additional lead placement.

The example of FIG. 5 includes anatomical dropzone 530 with a single lead designator for the lead(s) dropped in anatomical dropzone 530. In this example, anatomical dropzone 530 is located on the right side of the patient's head. If anatomical dropzone 530 has been assigned the maximum number of components that anatomical dropzone 530 can accommodate, then processor 390 may provide an indication of the maximum capacity being reached. In the example of FIG. 5, dropzone 530 includes a four-electrode lead, and can still accommodate another four-electrode leads. Hence, dropzone 530 is illustrated using a dashed-line border. For instance, if anatomical dropzone 530 reaches maximum capacity with respect to the assignable components, then processor 390 may "gray out" anatomical dropzone 530. For instance, the "graying out" may be in contrast to the illustrated dashed-line representation. As such, processor 390 may gray out anatomical dropzone 530 when any remaining lead is selected from area 520, to indicate that anatomical dropzone 530 is ineligible to receive the selected lead(s).

As illustrated in FIG. 5, UI 500 may also allow a user to indicate whether there are leads or other components that have been left in a patient that are no longer being used, i.e., that are not connected to the stimulation generator, which can be referred to as having been "abandoned." The user may be allowed to specify the locations of such components in patient using anatomical dropzones 504 and 522-530. In some examples, option tray 502 may include a generic "abandoned component" representation that a user can drag or otherwise move to an appropriate anatomical dropzone, or a specific component representation that a user may select from a menu, e.g., as described below with respect to FIGS. 6-11. Specifying the location of abandoned components may be desired for at least some of the reasons as specifying the locations active components, e.g., so a clinician may know component identities and locations prior to medical imaging of the patient.

FIGS. 6-11 illustrate an example UI by which a user may select components of a medical device, such as a stimulation controller or can, and one or more components attachable to the can. In some examples, after selection of the components via UI 600, the user may specify the locations of the components via UI 500 of FIG. 5.

In the examples of FIGS. 6-11, connection map 602 illustrates the connections, or ports, available from a stimulator, such as a stimulator represented by stimulator representation 504 pre-selected by the clinician via UI 500 of FIG. 5. Different stimulators may be characterized by different headers, ports, and numbers of ports. In the specific example of UI 600 illustrated in FIG. 6, connection map 602 indicates that the header of the selected implantable stimulator representation 504 has two ports 604 and 606, with each port having eight electrical contacts being configured to attach to a total of eight (8) electrodes of a lead. The contacts of each of ports 604 and 606 are configured to connect to respective proximal contacts on a proximal end of the lead. The proximal contacts are coupled to electrodes at a distal end of the lead via conductors within the lead.

Option tray 620 displays a listing of available components and attachments that the clinician can attach to one or both of the implantable stimulator's ports that are illustrated in connection map 602. In the example of UI 600, the components and attachments are selectable from any of dropdown menus 608 or 609. Dropdown menu 608 lists various components and attachments (e.g., leads and extensions) that can be used for percutaneous stimulation. Dropdown menu 609 lists various components and attachments that can be surgically implanted to deliver stimulation.

Workspace 610 represents an area of UI 600 that the clinician can use to edit the components attached to the ports shown in connection map 602. In various instances, workspace 610 may also be referred to as a "sandbox" or "sandbox area" of UI 600 provided by one or more interactive tools of this disclosure. For instance, the clinician may drag and drop, click and drop, or otherwise move or position one or more components selected from option tray 620 (e.g., via dropdown menus 608 and 609) into workspace 610. Aspects of this disclosure may guide and enable the clinician to attach a selected component representation (alternatively, "snap on," "lock on," or "build on") to stimulator representation 504, which may illustrate the actual or planned connection of components to a stimulator implanted (or planned for implantation) into a patient. More specifically, the clinician may attach the positioned component(s) to a specific one of port representations 604 or 606 illustrated in connection map 602.

Figure 7:
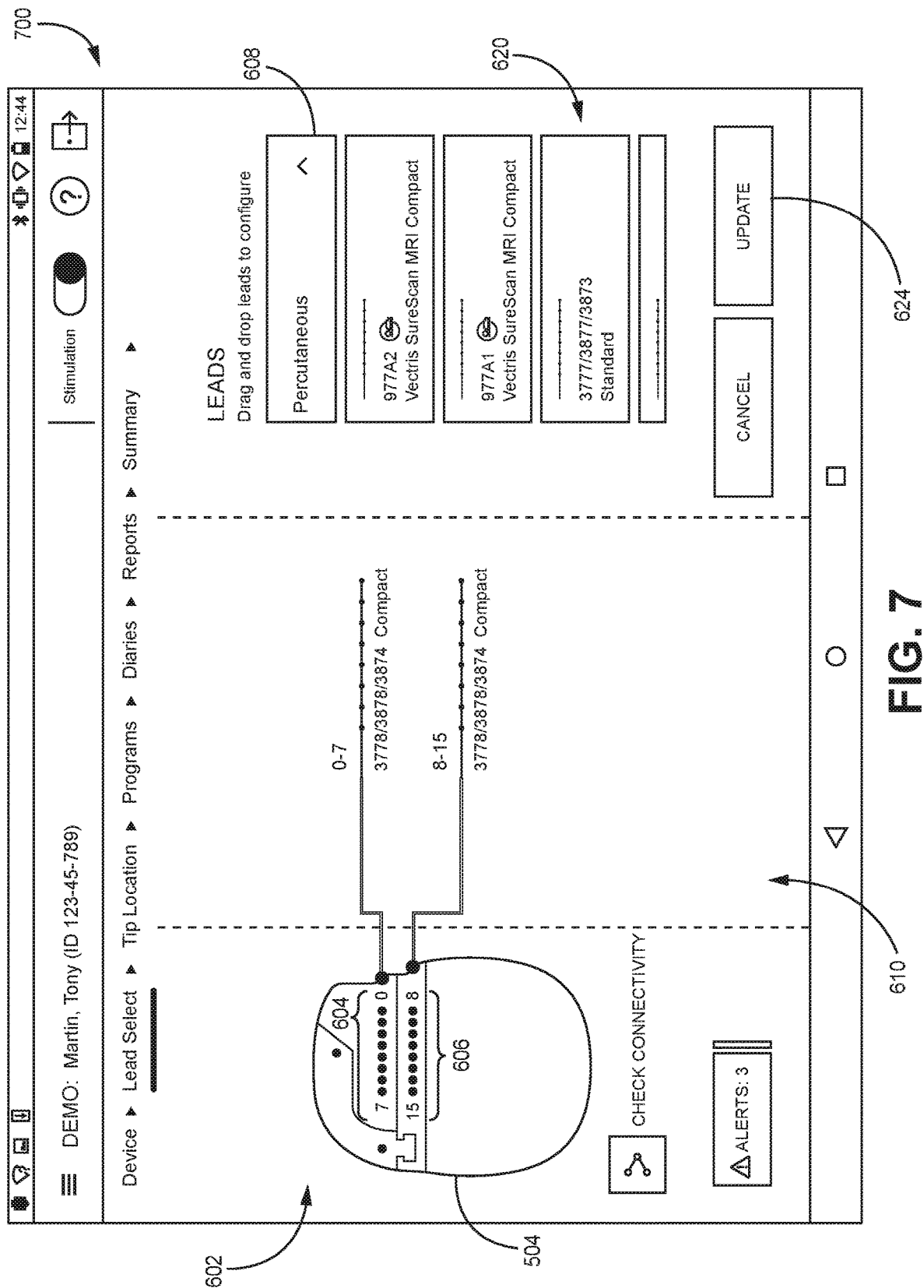

FIG. 7 illustrates UI 700, in which the clinician has activated dropdown menu 608 in order to select a percutaneous lead or extension. In the example of UI 700, option tray 620 lists various components from which a clinician can select for percutaneous stimulation, by way of dropdown menu 608. Examples of percutaneous stimulation components available via dropdown menu 608 include various lead models, such as the illustrated model "977A2" and "977A1" Vectris® MRI compatible leads, and the model 3777, 3877, and 3873 percutaneous leads, all available from Medtronic, PLC of Dublin, Ireland. As non-limiting examples, option tray 620 may offer various components such as a bifurcation extension, a cylindrical 1×8 lead, a cylindrical 1×4 lead, a paddle-shaped 1×4 lead, and so on. For instance, a 1×8 lead may include a total of eight (8) electrodes positioned inline, and a 1×4 lead may include a total of four (4) electrodes positioned inline. It will be appreciated that in other examples in accordance with this disclosure, option tray 620 may include differently-configured leads, and/or other different types of non-lead options, such as other multi-lead extensions and adapters.

Figure 6:
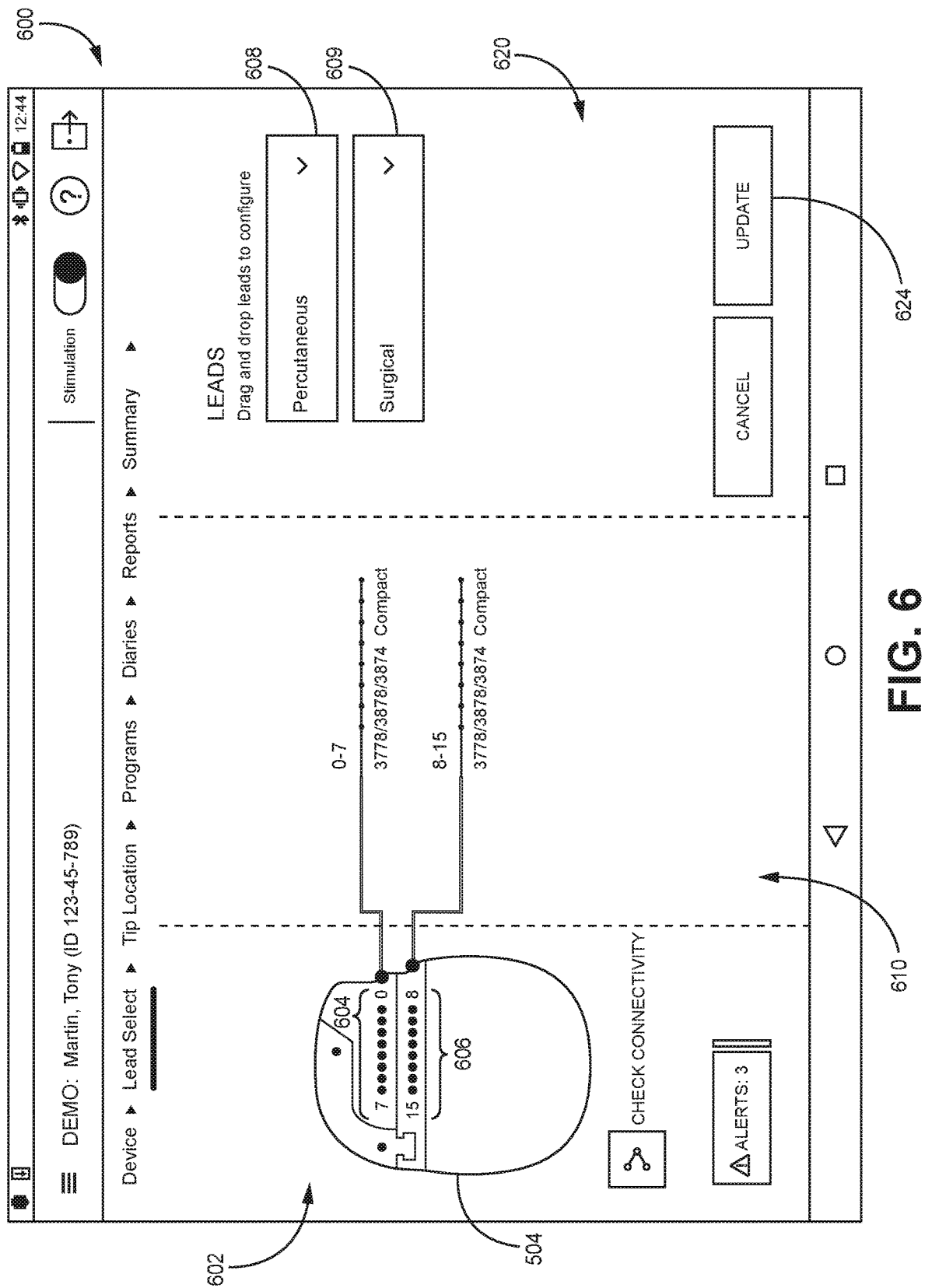

In the example of FIGS. 6 and 7, workspace 610 indicates that two 1×8 lead representations, e.g., corresponding to model 3778, 3878, 3874 compact percutaneous leads, all available from MedtronicPLC of Dublin, Ireland, are respectively coupled to the ports of stimulator representation 504. The illustrated lead representations may have been previously selected by a clinician from option tray 620, e.g., dropdown menu 608, and dragged into workspace 610. In other examples, the existing lead representations in workspace 610 may have been automatically pre-populated by the interactive UI 600, e.g., by processor 390 of programmer 24, based on, for example, the selected IMD representation 504 and/or an indication of the therapy to be delivered to the patient. In this manner, workspace 610 may provide indications of examples of leads that are compatible with stimulator 504.

By listing examples of compatible leads within option tray 620 and/or workspace 610, the interactive tools of this disclosure may guide a clinician in making appropriate choices when selecting one or more attachments for coupling to port 604 (e.g., by selecting a lead from dropdown menu 608). In other words, according to some implementations, the interactive tools of this disclosure may use workspace 610 to provide guidance to a clinician in selecting attachments for coupling to ports 604 and/or 606, while mitigating or potentially eliminating errors arising from incompatible attachment selections.

Figure 8:
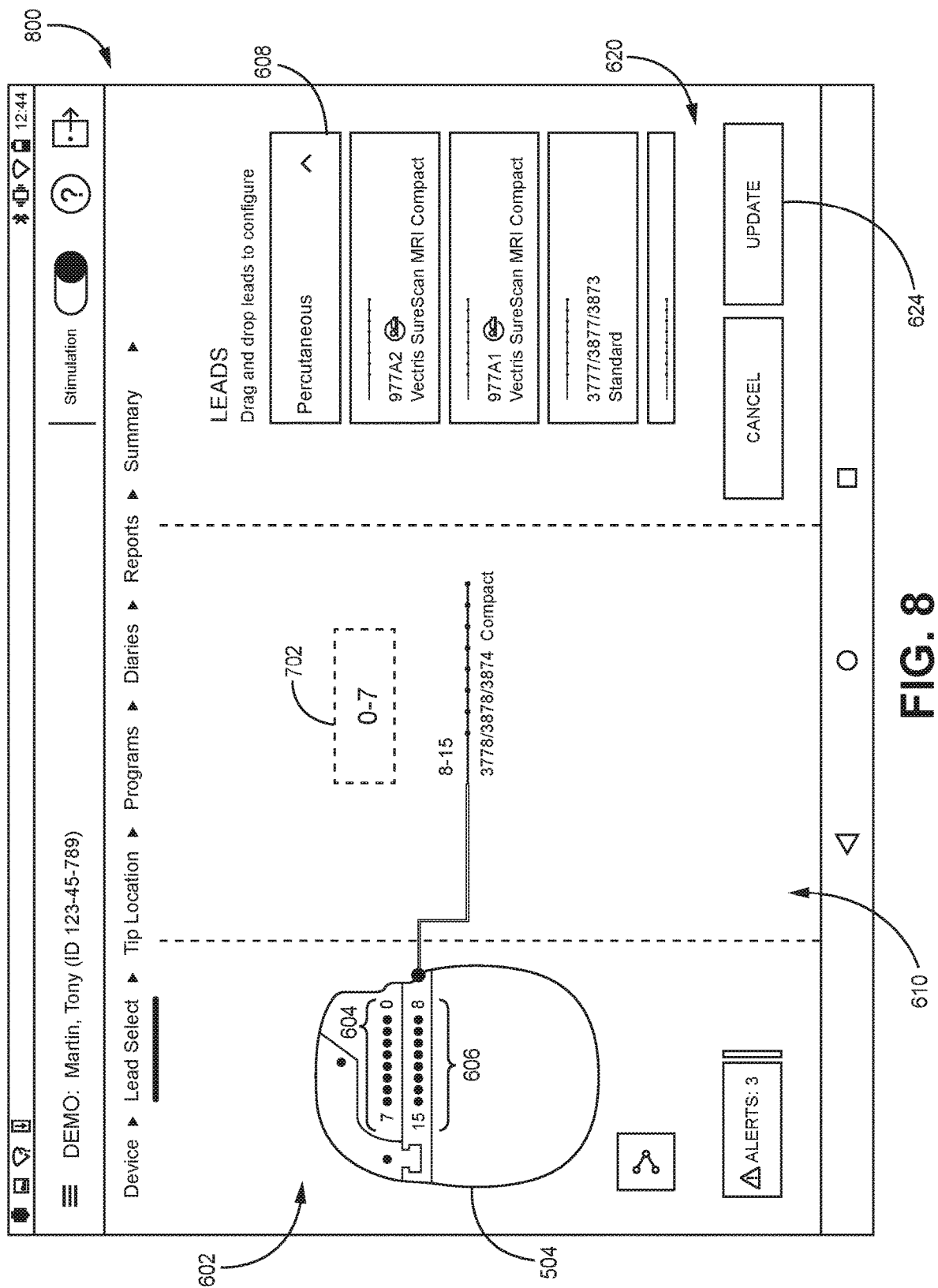

FIG. 8 illustrates a scenario in which port 604 of stimulator representation 602 is open, and UI 800 displays a dropzone 702 to guide selection and placement of a lead representation compatible with the open port. In the illustrated scenario, port 606 of stimulator representation is occupied by a lead representation, which may have been previously selected and positioned by the clinician. A clinician has activated dropdown menu 608 of option tray 620, from which the clinician may select an eight-electrode (e.g., a 1×8) lead. UI 800 may include eight electrode leads in dropdown menu 608 because port 604 provides eight electrical contacts.

Using UI 800, the clinician may drag or otherwise position a selected lead to a position within workspace 610. Based the eight-electrode characteristic of the leads available for selection, the interactive tools of this disclosure, e.g., as implemented by processor 390 of programmer 24, may link (or suggest linking) the lead to a particular port, or port(s) of stimulator 504 included in connection map 602. For example, processor 390 of programmer 24 may implement the interactive tools of this disclosure to provide a suggested area in which to drop a lead, once selected lead, within a certain proximity of a port. In the example of FIG. 8, processor 390 may provide dropzone guidance by suggesting a connection to port 604. In other implementations, processor 390 may provide multiple possible dropzones, such as a first dropzone corresponding to port 604 and a second dropzone corresponding to port 606, thereby providing the clinician with dropzone guidance for multiple port options. In some scenarios, if processor 390 determines that one of ports 604 or 606 is already connected to an attachment (e.g., that all eight contact points of the respective port are connected), then processor 390 may provide dropzone guidance only with respect to the remaining vacant port. In the illustrated example, dropzone 702 is called out using a dashed-line or dotted-line border, and includes an indication of the suggested port (which, in this case, is port 604). More specifically, in the particular implementation illustrated in FIG. 8, dropzone 702 includes an indication of the contact points (0-7) of the suggested port 604 of stimulator 504. In general, dropzone 702 is an example of a suggestion or prompt to a clinician that representative stimulator 504 includes an open port 604, and a suggestion to the clinician of how to indicate the connection of a lead, adaptor, catheter, or extension to the open port.

By including the term "0-7" in dropzone 702, one or more processors of programmer 24 may implement the interactive tools of this disclosure to provide an indication that, if the selected eight-electrode lead is dropped in dropzone 702, then the dropped lead would be snapped on to the port that includes contact points labeled "0-7," which in this example is the upper port (port 604) of stimulator representation 504. For instance, if the clinician drops a representation of an eight-electrode lead in dropzone 702, then one or more processors of programmer 24 that implement the interactive tools of this disclosure may snap the dropped lead representation to port 604 of stimulator representation 504, e.g., by forming a connection between the distal end of the upper port and the proximal end of the dropped lead. The illustrated connection may illustrate an actual or planned connection of a component and a stimulator implanted (or planned for implantation) in a patient.

As such, the placement of dropzone 702 and the dynamic updating of dropdown menu 608 illustrate techniques of this disclosure that programmer 24 may use to intuitively inform subsequent programming interfaces. As examples, programmer 24 may limit or populate the contents of dropdown menus 608 and/or 609 based on prior selections of leads and attachments that are logically connected to one or both of ports 604 and 606. Thus, programmer 24 may configure and/or constrain subsequent interfaces (and options presented therein) intuitively, based on logical connections represented in UI 800.

Another example of the dynamic updates that the interactive tools of this disclosure may implement is illustrated by the omission of dropdown menu 609 from option tray 620 in the use-case scenario of FIG. 8. More specifically, the interactive tools of this disclosure may dynamically omit dropdown menu 609 (which is directed to percutaneous leads and extensions) from UI 800, based on determining that the clinician has already connected an implantable lead to simulator 504. In this manner, the interactive tools of this disclosure may omit dropdown menu 609 from option tray 620, based on incompatibilities between implantable and percutaneous attachments if coupled to a common stimulator.

Figure 9:
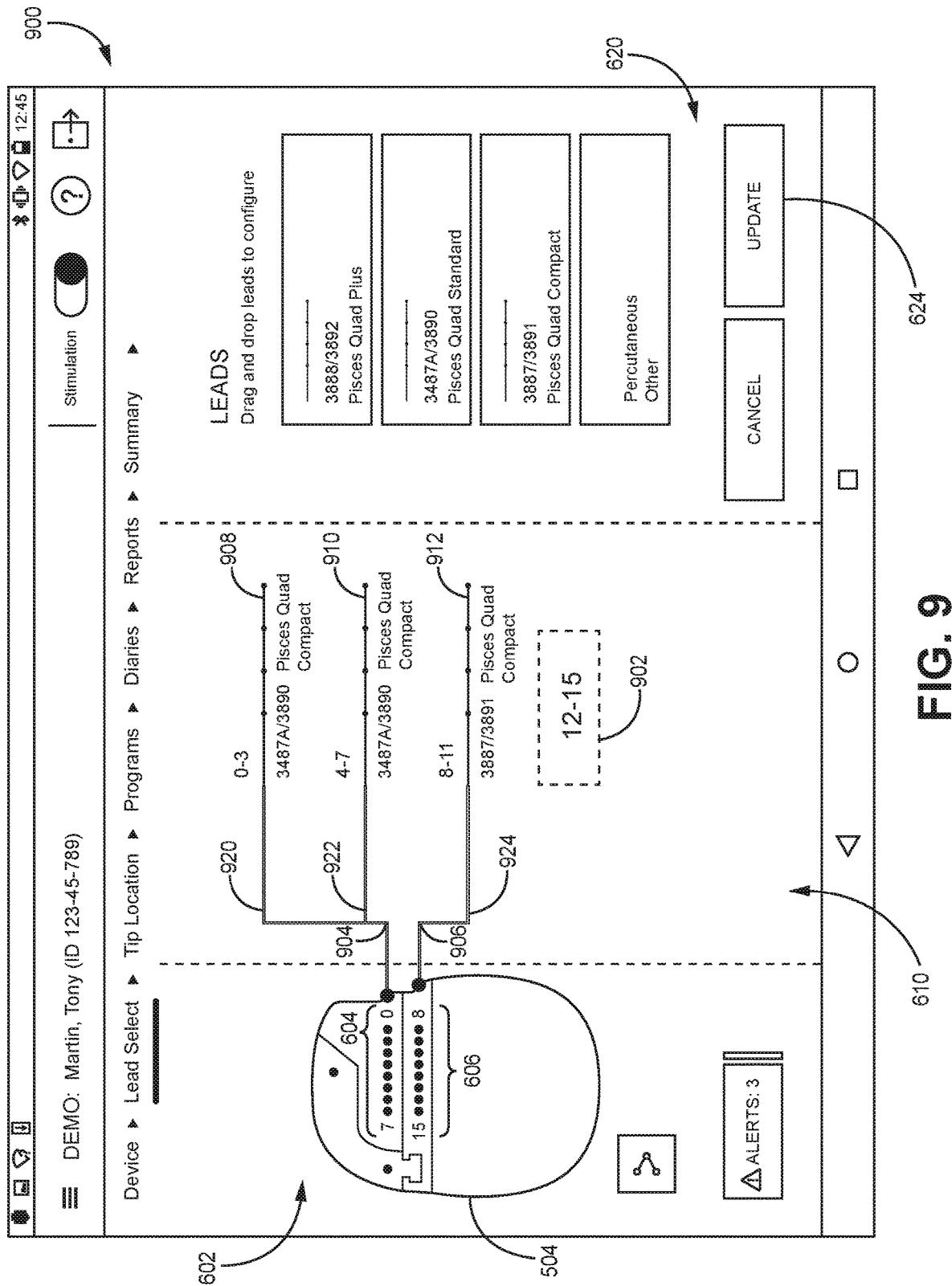

FIG. 9 illustrates UI 900, in which the clinician has used the interactive tools of this disclosure to specify the connection of several leads to ports 604 and 606. In the example of FIG. 9, the clinician has connected two 1×4 leads (908 and 910) onto port 604, and a single 1×4 lead (912) on to port 606. More specifically, the clinician may snap a bifurcation extension 904 and a bifurcation extension 906 on to each of ports 604 and 606, respectively, to enable the connection of two four contact leads to each of two eight-contact ports. In the implementation shown in FIG. 9, processor 390 displays ports 920 and 922 of bifurcation extension 904 and port 924 of bifurcation extension 906, all of which are coupled to attachments, and displays a dropzone (associated with contact points numbered "12-15") for a port that is not coupled to an attachment. In other implementations, processor 390 may display the "empty" port(s) of either of bifurcation extensions 904 or 906. For instance, according to the use-case scenario of FIG. 9, processor 390 may display an arm of bifurcation extension 906, with an indication that four contact points are still available to be used, via bifurcation extension. In turn, the clinician may snap an individual 1×4 lead of leads 908-912 on to each port of either bifurcation extension 904 or 906, thereby connecting each of 1×4 leads 908-912 to one of ports 604 or 606.

Each port of bifurcation extension 904 or bifurcation extension 906 may be configured to receive a lead or other extension, in a manner similar to ports 604 and 606 of stimulator 504. As used herein, the expression "snap on" may represent the formation of a logical connection between the representations of a component and a port, or between two component representations, which in turn may reflect the actual or planned physical connections of IMD components. For example, by snapping bifurcation extension 904 on to port 604, the clinician may form a logical connection between port 604 and the bifurcation extension. The connection between port 604 and bifurcation extension 904 represents a port-to-component snap on, according to the aspects of this disclosure. Processor 390 of programmer 24 may use the logical connection of port 604 to formulate dynamic catalogs associated with dropdown menus 608 and/or 609. For instance, processor 390 may identify various leads and/or attachments that can be connected to port 606, based on compatibility with the current logical connection(s) associated with port 604.

Additionally, the logical connection between leads 908 and 910 and the individual ports 920 and 922 at the distal ends of bifurcation extension 904 represents a component-to-component snap on, according to various aspects of this disclosure. Another example of a component-to-component snap on is the illustrated logical connection between the distal contacts of an extension component and the proximal contacts of a lead.

In some implementations, the processor(s) of programmer 24 may implement the interactive tools of this disclosure to run a "smart" algorithm, also referred to at various times as an "intelligent" or "intuitive" algorithm. For instance, programmer 24 may dynamically update option tray 620 to omit attachments that are incompatible with the current (e.g., incomplete) configuration of stimulator 504. In the example of UI 900, programmer 24 has updated option tray 620 such that option tray 620 only includes leads of the "Pisces Quad" family. For instance, the leads of the Pisces Quad family may represent 1×4 leads. As shown, only four contacts (of port 606, in this case) are vacant in terms of connections, in the scenario illustrated in FIG. 9. In the implementation illustrated in FIG. 9, the vacant connections are shown by way of dropzone 902, which prompts or provides a suggestion to the clinician to connect a 4-electrode lead via bifurcation extension 906. In other implementations, processor 390 may display an unused port (e.g., a second port positioned below port 924) of bifurcation extension 906, to indicate to the clinician that four contacts are still vacant and accessible via bifurcation extension 906. Thus, programmer 24 may limit the offered components of option 620 to four-electrode leads or attachments.

Additionally, programmer 24 may output dropzone 902 within proximity of port 606. By positioning dropzone in range of port 606 and port 924 of bifurcation extension 906, programmer 24 may guide the clinician to drop any selected 1×4 lead in workspace 610 such that the dropped lead snaps on to the only available contacts (in this case, contacts numbered "12-15" of port 606). For instance, if the clinician drops a selected 1×4 lead in dropzone 902, then processor 390 of programmer 24 may snap the dropped lead onto a bottom prong or bottom port of bifurcation extension 906, thereby forming a connection between the four contacts of dropped lead and contact numbered "12-15" of port 606.

In some use-case scenarios, processors 390 may display multiple dropzones, based on the availability of multiple available ports. As an example, if bifurcation extensions 904 and 906 are snapped on to ports 604 and 606, but no lead is attached to ports 920, 922, or 924 (in addition to the vacant bottom port of bifurcation extension 906), then processor 390 may display multiple dropzones within workspace 610. For instance, processor 390 may display four dropzones, with the dropzones being associated with contact points numbered 0-3, 4-7, 8-11, and 12-15, respectively. Once lead 908 is snapped onto port 920, processor 390 may update workspace 510 by reducing the number of dropzones to three (e.g., by removing the dropzone for contact points 0-3), and so on.

In some implementations of running the underlying smart algorithm of the interactive tools, programmer 24 may dynamically repopulate option tray 620 if the clinician removes (or "unsnaps") an attachment from one of ports 604 or 606 in workspace 610. For example, programmer 24 may dynamically present additional options (e.g., leads and/or other attachments) that are compatible with the updated configuration of stimulator 504, or may exclude some options based on incompatibility with the updated configuration of stimulator 504. To implement one or more configuration updates reflected in workspace 610, the clinician may click on update button 624 of UI 900.

In other examples, such as in scenarios where programmer 24 runs one or more of the smart algorithms of this disclosure, programmer 24 may automatically drag a bifurcation extension (or "bifucator") into workspace 610 for connecting to one of ports 604 or 606. In one example, programmer 24 may implement the smart algorithm to determine that port 606 is configured to receive one or more leads that provide a total of eight (8) electrodes, and that the clinician has dragged a 4-electrode lead into workspace 610. Based on this determination, programmer 24 may implement the smart algorithm to link (or suggest linking) a bifurcation extension to port 606. More specifically, the bifurcation extension may be required for the clinician to later complete the port 606 attachment(s) to include a total of eight electrodes, as is required due to the configuration of port 606.

In another example, programmer 24 may run the smart algorithm to determine that no single lead of the leads currently available from option tray 620 provides at least eight electrodes. Thus, in this scenario, the clinician may need to select multiple leads from option tray 620 in order to complete the port 606 attachments. Based on this determination, programmer 24 may implement the interactive tool to automatically place a bifurcation extension in workspace 610, regardless of whether or not the clinician has dragged any leads into workspace 610 for connection to port 606. In this case, programmer 24 may automatically snap the bifurcation extension to port 606, based on determining that port 606 includes the eight unused connection points, and that option tray 620 provides, at the time, only four-contact attachments. In this manner, programmer 24 may implement a smart algorithm of the interactive tools of this disclosure in a variety of ways to suggest or adaptively update workspace 610. A bifurcation extension as used above is understood to be a distally-bifurcating extension, in that the examples discussed above divide a single proximal connection (at a port of stimulator 504) into two distal connections shown in workspace 610.

In various examples, the interactive tool provided by the techniques of this disclosure may enable the clinician to "swap" leads and other attachments using interactive UIs 600-1000. For instance, the clinician may swap leads between port 604 and port 606, by dragging a lead that is currently attached to port 604, to snap onto port 606. In this example, programmer 24 may implement the interactive tool to automatically move the lead that was originally connected to port 606, to now be connected to port 604. In another example, the clinician may swap leads that are connected to bifurcation extension 904. For instance, in response to a clinician dragging a lead from one prong of bifurcation extension 904 to the other prong, programmer 24 may implement the interactive tool to swap the leads between the two prongs of bifurcation extension 904.

Additionally, the interactive tool may enable the clinician to move entire groupings of leads from one port to another, or to remove the grouping(s) from workspace 610. For instance, described with respect to UI 900 illustrated in FIG. 9, the clinician may drag the entire grouping connected to port 604, namely, bifurcation extension 904 with both attached leads 908 and 910, to disconnect the entire grouping from port 604. Thus, the interactive tools of this disclosure may enable the clinician to drag an intermediate connection (in this case, bifurcation extension 904) to move the intermediate connection with all downstream connections as a group. As used herein, the term "downstream" describes a connection that is connected, directly or indirectly, to an intermediate connection, such that the intermediate connection is positioned between the downstream connection and the can header of stimulator 504. In the example of FIG. 9, bifurcation extension 904 represents an intermediate connection, with both of 1×4 leads being downstream connections of bifurcation extension 904.

Described according to a tree structure, the interactive tools of this disclosure enable the clinician to drag a "root node" (in this case, bifurcation extension 904), along with all of the root node's respective leaf nodes (in this case, the 1×4 leads 908 and 910) as a group, rather than moving the group on a component-by-component basis. Aspects of the interactive tool of this disclosure may thus be described as being analogous to the use of interlocking and detachable building blocks, such as the toy construction bricks manufactured and marketed by the Lego® Group. In some examples, the interactive tool of this disclosure may be described as a block builder simulation tool in the context of electrical stimulators, with ports, leads, extensions and the like serving as building blocks.

Figure 10:
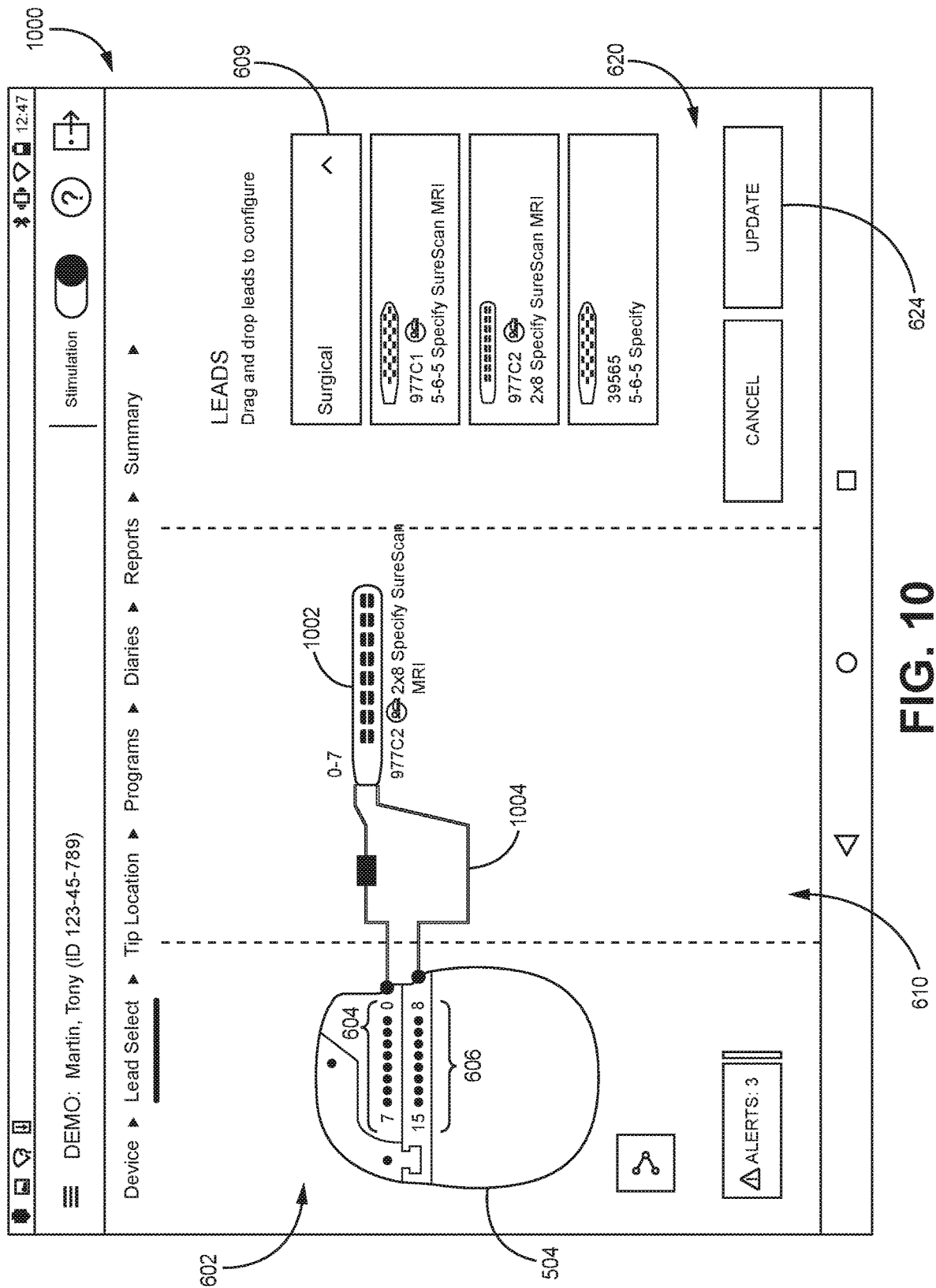

FIG. 10 illustrates UI 1000, in which a 2×8 surgical lead representation 1002 is connected to both of ports 604 and 606, via a proximally-bifurcating extension 1004. In the case of UI 1000, the clinician may select from any the sixteen-contact leads presented in dropdown menu 609, to connect via proximally-bifurcating extension 1004. In various examples, programmer 24 may update option tray 620 such that only sixteen-contact leads are offered via dropdown menu 610, based on proximally-bifurcating extension 1004 already being connected to ports 604 and 606 of stimulator 504. Examples of sixteen-contact leads offered via option tray 620 include 2×8 leads and 5-6-5 leads, the latter of which include contacts arranged in three rows of five, six, and five.

The clinician may use update button 624 to indicate the configuration of stimulator 504 is complete. In turn, because the connection points of stimulator representation 504 are fully occupied (i.e., each port is connected to a total of eight electrodes), programmer 24 may replace option tray 620 with another panel, such as a connection testing panel.

Figure 11:
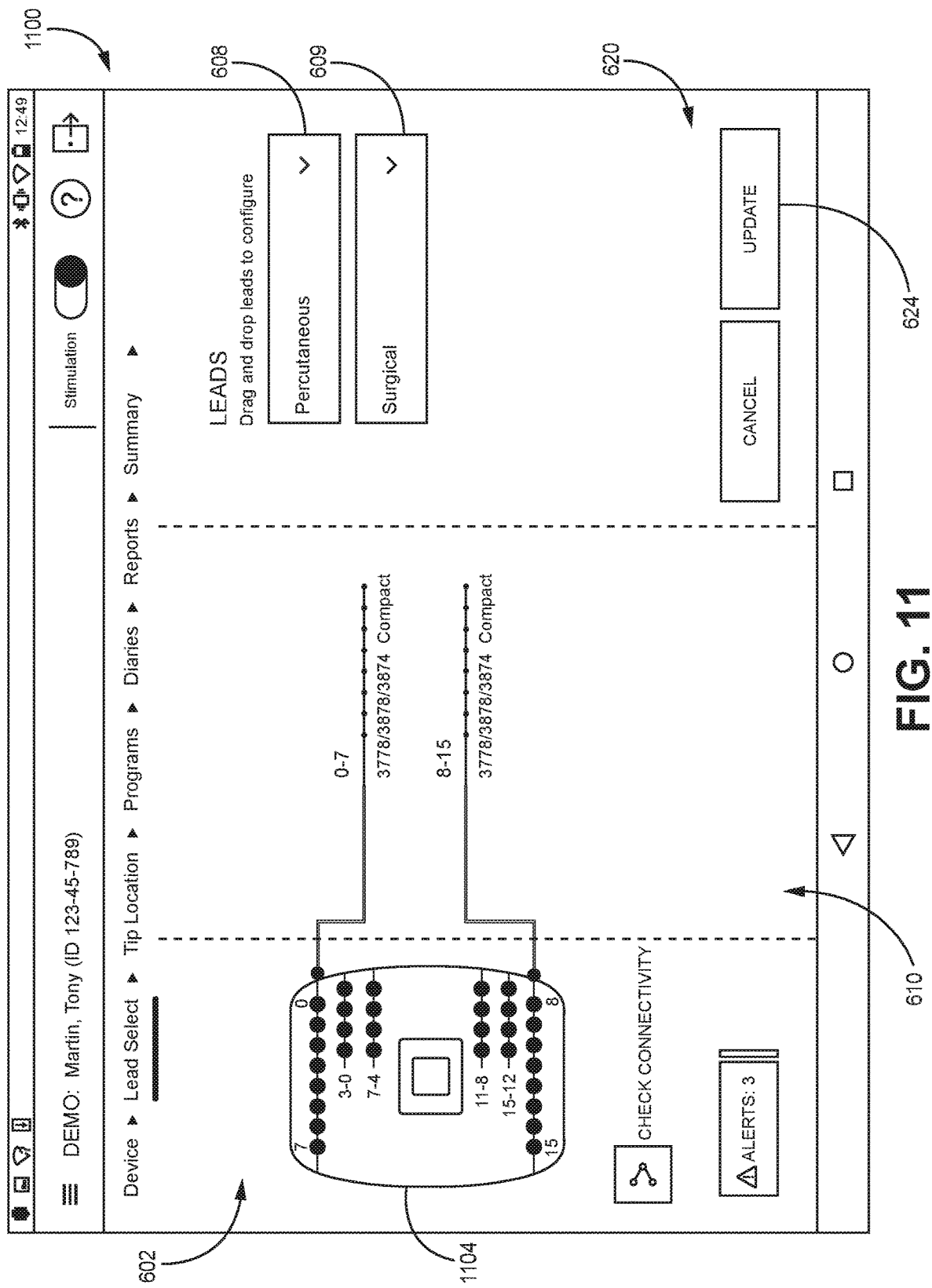

FIG. 11 illustrates UI 1100, which includes a representation of an external stimulator 1104 in connection map 602. UI 1100 is similar to UI 600 of FIG. 6, but applies to external stimulator 1104 instead of stimulator 504, which may be an example of an implantable device. External stimulator 1104 provides the clinician with variable port options, such as a pair of 4-connection ports that may supplant the use of a corresponding 8-connection port.

In various implementations, the interactive tool of this disclosure may auto-populate dropdown menus 608 and/or 609 based on different types of data. As one example, the interactive tool may auto-populate dropdown menus 608 and/or 609 based on attachments that are compatible with a particular selected stimulator, the can header of which is mapped in connection maps 502 and 602. Additionally, dropdown menus 608 and/or 609 may function as "dynamic catalogs" with respect to the selected stimulation device (e.g., stimulator 504). Aspects of this disclosure provide for various types of components to be provided via dropdown menus 608 and/or 609, including percutaneous extensions (in the case of an ENS), cervical extensions, adapters, etc. In some examples, the interactive tool may populate dropdown menus 608 and/or 609 based on previous screens or clinician selections, such as by populating or depopulating dropdown menus 608 and/or 609 dynamically to comport with the current device construction designs shown in respective workspaces 610.

Figure 12:
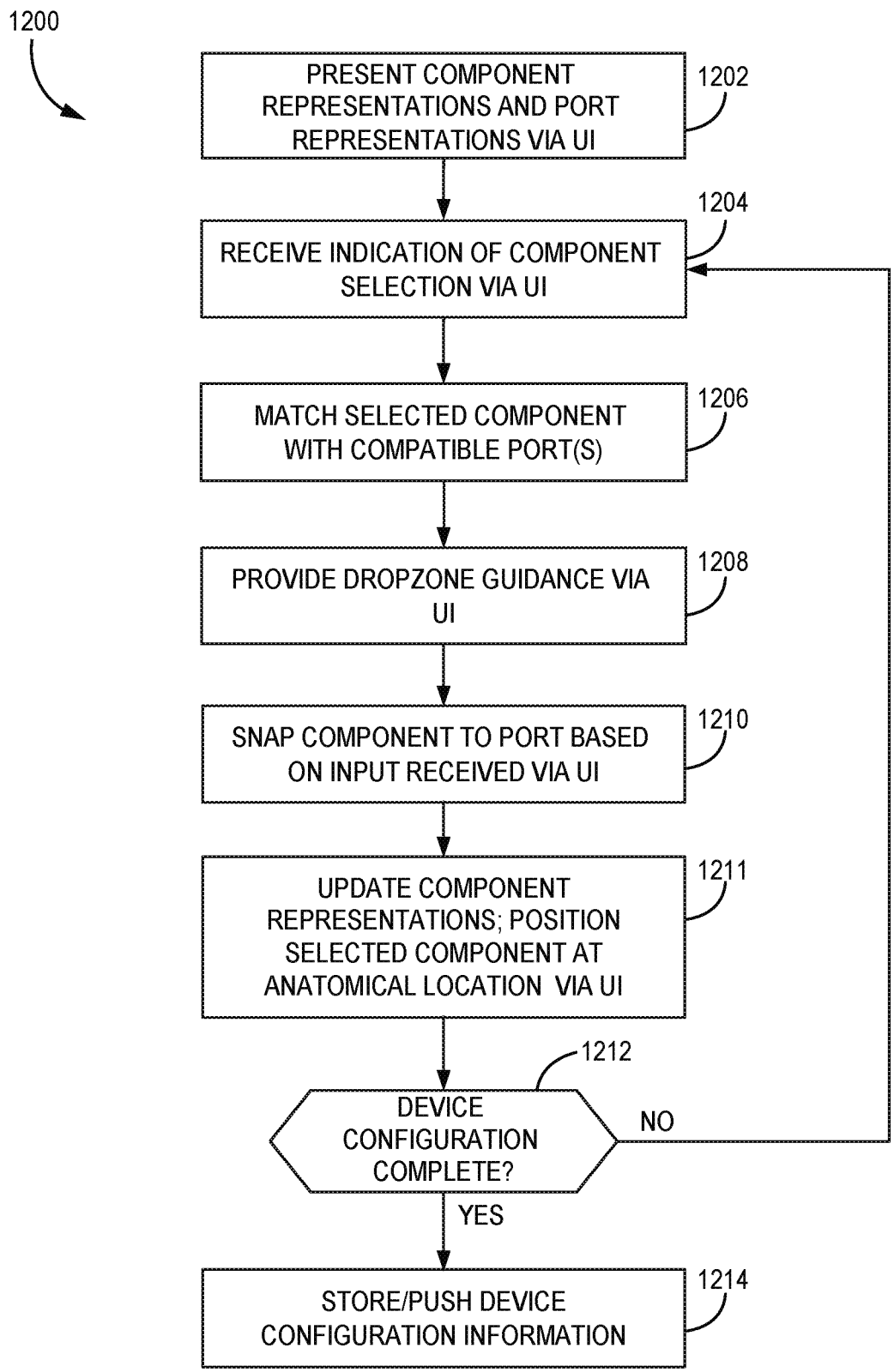
FIG. 12 is a flowchart illustrating a process that one or more computing devices may perform, in accordance with the techniques of this disclosure

FIG. 12 is a flowchart illustrating a process 1200 that one or more computing devices may perform, in accordance with the techniques of this disclosure. Process 1200 may begin when a computing device presents one or more component representations and port representations via a UI (1202). For instance, the computing device may output UI 600 of FIG. 6, which includes representations of ports 604 and 606 in component map 602 and representations of various components (e.g., leads and attachments) in dropdown menus 608 and 609 of option tray 620. The computing device may receive an indication of a component selection via the UI (1204). For instance, the computing device may receive a user input selecting a lead from one of dropdown menus 608 or 609, and dragging the lead into workspace 620.

The computing device may match the selected component with one or more compatible ports represented in the UI (1206). To match a selected component to a port, the computing device may determine whether the selected lead has a number of contacts that matches the number of contacts of each of ports 604 and 606. In some examples, the computing device may provide tools to enable compatibility, such as by automatically snapping a distal bifurcator onto a port, in order to enable the attachment of a selected four-electrode lead to an eight-contact port. Additionally, the computing device may provide dropzone guidance via the UI (1208). For instance, the computing device may display dropzone 702, to assist the clinician in placing the selected component (1210). The computing device may display varying numbers of dropzones, based on the number of vacant ports and/or the number of unused connection points at a given port. For instance, the computing device may output two dropzones, each corresponding to four connection points. As such, the number of dropzones displayed may vary, depending on the number of ports that still remain to be connected, or on the type of adaptor, or various other factors. For instance, a bifurcation extension may result in two drop zones (with 4 connection points each) per port being displayed, whereas only one drop zone (with 8 connection points) would be displayed without the bifurcation extension. By displaying dropzone 702, the computing device may implement one or more techniques of this disclosure to guide a clinician or provide viable options with respect to connecting the selected component (e.g., lead) to the stimulator 504.

Additionally, the computing device may update the component representations presented via the UI and position the selected components at anatomical locations (1211). For instance, the computing device may limit the remaining component representations so as to constrain the available options to those components that are compatible with the component(s) snapped on to the port at step 1210. Additionally, the computing device may position the selected components in workspace 510 or 610, using dropzone guidance provided via anatomical dropzones 522-530 or dropzones 702 and 802. In turn, the computing device may determine whether the device configuration has been completed, with respect to the current representation of a medical device that is output via the UI (1212). For instance, the computing device may determine whether update button 624 has been actuated via the UI. If the computing device determines that the device configuration is not yet completed for the instant representation ('NO' branch of 1212), then the computing device may receive or await receipt of any further indications of component selections via the UI (thereby returning to step 1204). However, if the computing device determines that the device configuration has been completed for the instant representation ('YES' branch of 1212), then the computing device may store the configuration information (1214). In some examples, the computing device, which may be a programmer, may push or propagate the configuration to a medical device, such as stimulator 504 as by one or more telemetry transmissions.

The clinician may configure an implantable stimulator or ENS using interactive tools of this disclosure at various stages, such as pre-operative, intra-operative, or post-operative stages of use. For instance, at a planning or "pre-op" stage, the clinician may use the interactive tool to design a construction and configuration the stimulator for future usage (e.g., how an implantable stimulator will be implanted at a later time). In other words, the clinician may configure the stimulator at the pre-op stage to propagate the configuration into later stages of usage of the stimulator. In some examples, the clinician may store a set of device configurations, enabling himself/herself or other clinicians to select a pre-built configuration with which to configure an IMD or ENS in the future. For instance, the clinician may use interactive tools of this disclosure to configure representations of medical devices. In turn, clinicians may draw upon configurations of these device representations in order to configure devices at a later stage.

At an "intra-op" stage, e.g. during the implantation procedure, the clinician may use the interactive tool to record the configuration of the stimulator. At a "post-op" stage, e.g., after an implantable stimulator has been implanted, the clinician may use the interactive tool of this disclosure to identify, document, audit, or edit the performance of the stimulator.

Additionally, the clinician may use the interactive tool to configure a stimulator either in communication with the stimulator, or offline from the stimulator. For instance, if the computing device running the interactive tool is currently in communication with the stimulator, the clinician may use the interactive tool to perform real-time (or almost real-time) configuration of the stimulator. In scenarios where the computing device running the interactive tool is offline from the stimulator, the clinician may formulate the construction and/or configuration using the interactive tool, and later "plug in," "drive," or propagate the pre-formulated construction/configuration to one or more stimulators, such as an off-the-shelf stimulator.

Depending on various attributes of the computing device that runs the interactive tool, the clinician may perform various actions to "drag" components. For instance, if the clinician uses the interactive tool from a desktop or laptop computer, the clinician may click on and hold a selected component or group using a mouse or trackpad, and use the mouse or trackpad to adjust the position of the selected component(s). If the clinician uses a touchscreen-based device, such as a tablet computer or smartphone, the clinician may click on and hold a selected component or group using a stylus or a finger, and use the stylus or finger to adjust the position of the selected component(s). In some implementations, the interactive tool may enable the clinician to click on a component to select the component, and click on a particular destination, to place the selected component at the destination. According to the "click to select" implementation described above, the interactive tool may enable the clinician to configure the system without a need to drag and drop using an input device such as a mouse, trackpad, or touchscreen.

Additionally, once an IMD or ENS is configured using the interactive tool of this disclosure, then various stimulation programming systems compatible with the medical device may present programming options for the so-configured IMD or ENS. For instance, the stimulation programming systems may implement additional interactive UIs via the clinician programmer or patient programmer, by which the user can effect programming changes with respect to the configured medical device. As some non-limiting examples, the stimulation programming systems may present data for the same types of leads and/or electrodes that are included in the configured medical device, thereby enabling the user to program the corresponding lead(s) and/or electrode(s).

In various examples, this disclosure is directed to a method for configuring a representation of a medical device. The method includes presenting, by a computing device, via a user interface (UI), a representation of the medical device and respective representations of one or more components that are attachable to the medical device, wherein the one or more components comprise at least one of leads, adaptors, extensions, or catheters. The method further includes receiving, by the computing device, via the UI, an indication of a selected component included in the one or more components for attachment to the medical device. The method further includes, responsive to receiving the indication of the selected component: indicating, by the computing device and via the UI, attachment of the representation of the selected component to the representation of the medical device, and updating, by the computing device, the presentation of the respective representations of the one or more components via the UI to include representations of one or more components that are attachable to the medical device with the selected component. In some examples, presenting the representation of the medical device includes displaying, by the computing device, the representation of the medical device in a first area of the UI, presenting the respective representations of the one or more components includes displaying, by the computing device, the respective representations of the one or more components in a second area of the UI, updating the presentation of the respective representations of the one or more components via the UI includes updating, by the computing device, the second area of the UI, the method further comprising presenting a third area of the UI. In some examples, receiving the indication of the selected component for attachment to the medical device includes receiving user input that indicates repositioning of the representation of the selected component from the second area to the third area, and indicating attachment of the representation of the selected component to the representation of the medical device includes indicating an attachment from the representation of the selected component in the third area to the representation of the medical device in the first area.

In some examples, the method further includes presenting, by the computing device, via the UI, an indication of one or more dropzones for the selected component in the third area, wherein each of the one or more dropzones is associated with a respective port the medical device or a previously selected component attached to the medical device. In some examples, presenting the dropzone includes presenting and configuring the dropzone to indicate that the associated port is compatible with the selected component. In some examples, determining, by the computing device, whether the selected component is compatible with the port of the medical device by comparing a number of electrodes associated with the selected component to a number of electrodes associated with the port. In some examples, indicating attachment of the representation of the selected component to the representation of the medical device includes presenting, by the computing device, via the UI, a link between the selected component and a first port of one or more ports associated with the medical device.

According to some examples, the method further includes determining, by the computing device, whether the selected component is compatible with each port of the one or more ports associated with the medical device, and forming, by the computing device, the link between the selected component and the first port based on determining that the selected component is compatible with the first port. In some examples, determining whether the selected component is compatible with each port of the one or more ports includes comparing a number of electrodes associated with the selected component to a respective number of electrodes associated with each port of the one or more ports. According to some examples, a first component of the one or more components is an extension having a port configured to receive a second component, and updating the presentation of the respective representations of the one or more components includes limiting the presentation of the respective representations to represent only components that are compatible with the port of the extension. In some examples, the extension is a distal bifurcator that bifurcates into two ports. In some examples, the extension is a proximal bifurcator that combines into a single port.

According to some examples, the method further includes presenting, by the computing device, via the UI, a representation of a patient body in conjunction with the representation of the medical device and the representation of the selected component. In some examples, the method further includes presenting, by the computing device, respective representations of one or more anatomical dropzones at respective positions on the representation of the patient body, wherein each respective representation of the one or more anatomical dropzones is based on a characteristic of the selected component. In some examples, the method further includes receiving, by the computing device, user input indicating positioning at least one of the representation of the medical device or the representation of the selected component at a respective one of the anatomical dropzones. According to some examples, the method further includes storing indications of locations for at least one of the medical device or the selected component in the patient based on the user input indicating the positioning.

In some examples, this disclosure is directed to a programming device for a medical device that includes a communication module configured to communicate with the medical device, a memory, a user interface (UI) configured to receive inputs and to output data, and one or more processors. The one or more processors are configured to present, via the UI, a representation of the medical device and respective representations of one or more components that are attachable to the medical device, wherein the one or more components comprise at least one of leads, adaptors, extensions, or catheters. The one or more processors are further configured to receive, via the UI, an indication of a selected component included in the one or more components for attachment to the medical device. The one or more processors are further configured to, responsive to receiving the indication of the selected component: indicate, via the UI, attachment of the representation of the selected component to the representation of the medical device, and to update the presentation of the respective representations of one or more components via the UI to include representations of one or more components that are attachable to the medical device with the selected component. In some examples, this disclosure is directed to a system that includes a medical device configured to deliver one or both of electrical signals or one or more therapeutic agents, and a programming device configured to communicate with the medical device. The programming device includes one or more processors. The processors(s) of the programming device are configured to present, via a user interface (UI), a representation of the medical device and respective representations of one or more components that are attachable to the medical device, wherein the one or more components comprise at least one of leads, adaptors, extensions, or catheters, and to receive, via the UI, an indication of a selected component included in the one or more components for attachment to the medical device. The processor(s) of the programming device are further configured to, responsive to receiving the indication of the selected component: indicate, via the UI, attachment of the representation of the selected component to the representation of the medical device, and to update the presentation of the respective representations of one or more components via the UI to include representations of one or more components that are attachable to the medical device with the selected component.

According to some examples, to present the representation of the medical device, the processor(s) of the programming device are configured to display the representation of the medical device in a first area of the UI. In some examples, to present the respective representations of the one or more components, the processor(s) of the programming device are configured to display the respective representations of the one or more components in a second area of the UI. According to some examples, to update the presentation of the respective representations of the one or more components via the UI, the processor(s) of the programming device are configured to update the second area of the UI, the processor(s) of the programming device being further configured to present a third area of the UI.

In some examples, to receive the indication of the selected component for attachment to the medical device, the processor(s) of the programming device are configured to receive user input that indicates repositioning of the representation of the selected component from the second area to the third area, and to indicate attachment of the representation of the selected component to the representation of the medical device, the processor(s) of the programming device are configured to indicate an attachment from the representation of the selected component in the third area to the representation of the medical device in the first area. According to some examples, the processor(s) of the programming device are further configured to: present, via the UI, an indication of one or more dropzones for the selected component in the third area, where each of the one or more dropzones is associated with a respective port the medical device or a previously selected component attached to the medical device.

According to some examples, to present the dropzone, the processor(s) of the programming device are configured to present and configure the dropzone to indicate that the associated port is compatible with the selected component. In some examples, the processor(s) of the programming device are further configured to determine whether the selected component is compatible with the port of the medical device by comparing a number of electrodes associated with the selected component to a number of electrodes associated with the port. According to some examples, to indicate attachment of the representation of the selected component to the representation of the medical device, the processor(s) of the programming device are configured to present, via the UI, a link between the selected component and a first port of one or more ports associated with the medical device. In some examples, the processor(s) of the programming device are further configured to: determine whether the selected component is compatible with each port of the one or more ports associated with the medical device, and to form the link between the selected component and the first port based on determining that the selected component is compatible with the first port.

In some examples, to determine whether the selected component is compatible with each port of the one or more ports, the processor(s) of the programming device are configured to compare a number of electrodes associated with the selected component to a respective number of electrodes associated with each port of the one or more ports. According to some examples, the extension is a distal bifurcator that bifurcates into two ports. According to some examples, the extension is a proximal bifurcator that combines into a single port.

According to some examples, the processor(s) of the programming device are further configured to store the configured representation of the medical device as part of a set of medical device configurations to the memory. In some examples, the processor(s) of the programming device are further configured to select stimulation programming options via the UI based on the configuration. In some examples, the processor(s) of the programming device are further configured to receive user input for programming delivery of stimulation by the medical device based on the selected stimulation programming options. According to some examples, the processor(s) of the programming device are further configured to program the medical device to deliver stimulation according to the user input. In some examples, the medical device is configured to deliver a combination of electrical stimulation and the one or more therapeutic agents using a catheter that includes one or more electrodes.

In various examples, this disclosure is directed to a method for indicating or selecting a configuration of a medical device. The method includes presenting, via a user interface, a representation of one or more components that are attachable to the medical device, and receiving, via the user interface, a selection of a component to be attached to the medical device. The method may further include presenting, via the user interface, an updated representation of the medical device based on the selection of the component to be attached to the medical device. In some examples, the method may further include updating a list of the one or more components attachable to the medical device, based on the selection of the component to be attached to the medical device, and presenting, via the user interface, an updated representation of the one or more components that are attachable to the medical device. In some examples, the medical device may include an implantable medical device (such as stimulation controller 324). In some examples, the medical device may include an external neurostimulator (or "ENS").

In some examples, the one or more components may include at least one of a bifurcation extension, a cylindrical lead, or a paddle-shaped lead. In some examples, at least one of the cylindrical lead and the paddle-shaped lead includes one or more electrodes. Aspects of this disclosure are also directed to a programming device for a medical device including one or more processors configured to perform any of the techniques described herein, or any combination of the various techniques described herein. In some examples, the medical device includes an implantable medical device, such as stimulation controller 324.

The disclosure contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory that is tangible. The computer-readable storage media may be referred to as non-transitory. A programmer, such as patient programmer or clinician programmer, or other computing device may also contain a more portable removable memory type to enable easy data transfer or offline data analysis.

The techniques described in this disclosure, including those attributed to programmer 24, and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, remote servers, or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. For example, any of the techniques or processes described herein may be performed within one device or at least partially distributed amongst two or more devices, such as between programmer 24 and a server. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in an article of manufacture including a computer-readable storage medium encoded with instructions. Instructions embedded or encoded in an article of manufacture including a computer-readable storage medium encoded, may cause one or more programmable processors, or other processors, to implement one or more of the techniques described herein, such as when instructions included or encoded in the computer-readable storage medium are executed by the one or more processors. Example computer-readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or any other computer readable storage devices or tangible computer readable media. The computer-readable storage medium may also be referred to as storage devices.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

Various examples have been described herein. Any combination of the described operations or functions is contemplated. These and other examples are within the scope of the following claims.

What is claimed is:

1. A method for configuring a representation of a medical device, the method comprising:
   presenting, by a computing device, via a user interface (UI), a representation of the medical device and respective representations of each of a set of one or more components that are attachable to the medical device, wherein the set of components comprise at least one of leads, adaptors, extensions, or catheters;
   receiving, by the computing device, via the UI, an indication of a selected component from the set of components for attachment to the medical device;

responsive to receiving the indication of the selected component and based on which of the set of components is the selected component:
selecting, by the computing device, for presentation via the UI, respective indications of one or more compatible anatomical dropzones and one or more compatible port dropzones for the selected component, each respective anatomical dropzone representing an area on a representation of a patient body in which the selected component is implantable and each respective port dropzone representing a respective port either of the medical device or of a previously selected component attached to the medical device that is compatible for connection with the selected component, wherein the previously selected component, if attached to the medical device, is either a distal bifurcator that bifurcates into two extension ports or a proximal bifurcator that combines into a single extension port;
determining, by the computing device, that the selected component has been dropped at a location of the UI that corresponds to the respective representation of a particular port dropzone of the one or more compatible port dropzones;
associating, by the computing device, based on the location of the UI that corresponds to the respective representation of the particular port dropzone in which the selected component was dropped, the selected component with a first port corresponding to the particular port dropzone either of the medical device or of the previously-selected component attached to the medical device;
indicating, by the computing device and via the UI, attachment of the representation of the selected component to the representation of the medical device via the first port either of the medical device or of the previously selected component attached to the medical device;
identifying, based on the attachment of the selected component via the first port either of the medical device or of the previously selected component attached to the medical device, an updated set of one or more components that each has a configuration of electrical contact points attachable to the medical device with the attachment of the selected component via the first port either of the medical device or of the previously selected component attached to the medical device; and
updating, by the computing device, the presentation of the respective representations of the set of components via the UI to include only representations of the updated set of components that are attachable to the medical device with the attachment of the selected component via the first port either of the medical device or of the previously selected component attached to the device.

2. The method of claim 1,
wherein presenting the representation of the medical device comprises displaying, by the computing device, the representation of the medical device in a first area of the UI,
wherein presenting the respective representations of each of the set of components comprises displaying, by the computing device, the respective representations of each of the set of components in a second area of the UI,
wherein updating the presentation of the respective representations of the set of components via the UI comprises updating, by the computing device, the second area of the UI to include the representations of the updated set of components, the method further comprising presenting, by the computing device, a third area of the UI,
wherein receiving the indication of the selected component for attachment to the medical device comprises receiving user input that indicates repositioning of the representation of the selected component from the second area to the third area,
wherein presenting the respective indications of the one or more compatible anatomical dropzones and the one or more compatible port dropzones comprises presenting all of the respective indications in the third area, and
wherein indicating the attachment of the representation of the selected component to the representation of the medical device comprises indicating an attachment from the representation of the selected component in the third area to the representation of the medical device in the first area.

3. The method of claim 1, further comprising:
determining, by the computing device, that the selected component is compatible with the first port of the medical device by comparing a number of electrodes associated with the selected component to a number of electrodes associated with the first port.

4. The method of claim 1, wherein indicating the attachment of the representation of the selected component to the representation of the medical device comprises presenting, by the computing device, via the UI, a link between the selected component and the first port of one or more ports associated with the medical device, wherein the first port is associated with the respective particular port dropzone of the one or more compatible port dropzones.

5. The method of claim 4, further comprising:
determining, by the computing device, that the selected component is compatible with each port of the one or more ports associated with the medical device; and
forming, by the computing device, the link between the selected component and the first port based on determining that the selected component is compatible with the first port.

6. The method of claim 5, wherein determining that the selected component is compatible with each port of the one or more ports comprises comparing a number of electrodes associated with the selected component to a respective number of electrodes associated with each port of the one or more ports.

7. The method of claim 1, wherein the selected component of the set of components is an extension having a port configured to receive a second component, and wherein updating the presentation of the respective representations of the set of components comprises limiting the presentation of the representations of the updated set of components to represent only components that are compatible with the port of the extension.

8. The method of claim 7, wherein the distal bifurcator is a first distal bifurcator, wherein the two extension ports represent a first pair of extension ports, and wherein the extension is a second distal bifurcator that bifurcates into a second pair of extension ports.

9. The method of claim 7, wherein the proximal bifurcator is a first proximal bifurcator, wherein the single extension port is a first extension port, and wherein the extension is a second proximal bifurcator that combines into a single second extension port.

10. The method of claim 1, further comprising storing the configured representation of the medical device as part of a set of medical device configurations in a memory.

11. The method of claim 10, further comprising configuring the medical device based on the configured representation of the medical device.

12. The method of claim 11, further comprising delivering stimulation using the medical device as configured based on the configured representation.

13. The method of claim 1, further comprising:
selecting, by the computing device, stimulation programming options via the UI based on the configuration;
receiving user input for programming delivery of stimulation by the medical device based on the selected stimulation programming options; and
programming the medical device to deliver stimulation according to the user input.

14. The method of claim 13, wherein programming the medical device to deliver the stimulation according to the user input comprises customizing, based on the user input, one or more of an amplitude, a pulse width, a pulse rate, an electrode polarity, or an electrode combination associated with the stimulation.

15. A programming device for a medical device comprising:
communication circuitry configured to communicate with the medical device;
a memory configured to store data;
one or more output devices in communication with the memory, the one or more output devices being configured to output a user interface (UI) using the data stored to the memory;
one or more input devices in communication with the memory, the one or more input devices being configured to receive inputs and store the inputs as part of the data stored to the memory; and
processing circuitry in communication with the memory, the processing circuitry being configured to:
present, via the UI, a representation of the medical device and respective representations of each of a set of one or more components that are attachable to the medical device, wherein the set of components comprise at least one of leads, adaptors, extensions, or catheters;
receive, via the UI, an indication of a selected component from the set of components for attachment to the medical device;
responsive to receiving the indication of the selected component:
select for presentation via the UI, respective indications of one or more compatible anatomical dropzones and one or more compatible port dropzones for the selected component, each respective anatomical dropzone representing an area on a representation of a patient body in which the selected component is implantable and each respective port dropzone representing a respective port either of the medical device or of a previously selected component attached to the medical device is compatible for connection with the selected component, wherein the previously selected component, if attached to the medical device, is either a distal bifurcator that bifurcates into two extension ports or a proximal bifurcator that combines into a single extension port;
determine that the selected component has been dropped at a location of the UI that corresponds to the respective representation of a first port corresponding to the particular port dropzone either of the one or more compatible port dropzones;
associate, based on the location of the UI that corresponds to the respective representation of the particular port dropzone in which the selected component was dropped, the selected component with a first port either of the medical device or of the previously-selected component attached to the medical device;
indicate, via the UI, attachment of the representation of the selected component to the representation of the medical device via the particular port of the medical device or of the previously selected component attached to the medical device;
identify, based on the attachment of the selected component via the first port either of the medical device or of the previously selected component attached to the medical device, an updated set of one or more components that each has a configuration of electrical contact points attachable to the medical device with the attachment of the selected component via the first port either of the medical device or of the previously selected component attached to the medical device; and
update the presentation of the respective representations of the set of components via the UI to include only representations of the updated set of components that are attachable to the medical device with the attachment of the selected component via the first port either of the medical device or of the previously-selected component attached to the medical device.

16. The programming device of claim 15,
wherein to present the representation of the medical device, the processing circuitry is configured to display the representation of the medical device in a first area of the UI,
wherein to present the respective representations of each of the set of components, the processing circuitry is configured to display the respective representations of each of the set of components in a second area of the UI to include the representations of the updated set of components,
wherein to update the presentation of the respective representations of the set of components via the UI, the processing circuitry is are configured to update the second area of the UI,
the processing circuitry being further configured to present a third area of the UI,
wherein to receive the indication of the selected component for attachment to the medical device, the processing circuitry is configured to receive user input that indicates repositioning of the representation of the selected component from the second area to the third area,
wherein to present the respective indications of the one or more compatible anatomical dropzones and the one or more compatible port dropzones, the processing circuitry is configured to present all of the respective indications in the third area, and
wherein to indicate the attachment of the representation of the selected component to the representation of the medical device, the processing circuitry is configured to indicate an attachment from the representation of the selected component in the third area to the representation of the medical device in the first area.

17. The programming device of claim 15, wherein the processing circuitry is further configured to determine that the selected component is compatible with the first port of the medical device by comparing a number of electrodes associated with the selected component to a number of electrodes associated with the first port.

18. The programming device of claim 15, wherein to indicate the attachment of the representation of the selected component to the representation of the medical device, the processing circuitry is configured to present, via the UI, a link between the selected component and the first port of one or more ports associated with the medical device, wherein the first port is associated with the respective particular port dropzone of the one or more compatible port dropzones.

19. The programming device of claim 18, the processing circuitry being further configured to:
   determine that the selected component is compatible with each port of the one or more ports associated with the medical device; and
   form the link between the selected component and the first port based on determining that the selected component is compatible with the first port.

20. The programming device of claim 19, wherein to determine that the selected component is compatible with each port of the one or more ports, the processing circuitry is configured to compare a number of electrodes associated with the selected component to a respective number of electrodes associated with each port of the one or more ports.

21. The programming device of claim 15, wherein the selected component of the set of components is an extension having a port configured to receive a second component, and wherein to update the presentation of the respective representations of the set of components, the one or more processors are configured to limit the presentation of the representations of the updated set of components to represent only components that are compatible with the port of the extension.

22. The programming device of claim 21, wherein the distal bifurcator is a first distal bifurcator, wherein the two extension ports represent a first pair of extension ports, and wherein the extension is a second distal bifurcator that bifurcates into a second pair of extension ports.

23. The programming device of claim 21, wherein the proximal bifurcator is a first proximal bifurcator, wherein the single extension port is a first extension port, and wherein the extension is a second proximal bifurcator that that combines into a single second extension port.

24. The programming device of claim 15, wherein the processing circuitry is further configured to store the configured representation of the medical device as part of a set of medical device configurations to the memory.

25. The programming device of claim 15, wherein the processing circuitry is further configured to:
   select stimulation programming options via the UI based on the configuration;
   receive user input for programming delivery of stimulation by the medical device based on the selected stimulation programming options; and
   program the medical device to deliver stimulation according to the user input.

26. The programming device of claim 25, wherein to program the medical device to deliver the stimulation according to the user input, the processing circuitry is configured to customize, based on the user input, one or more of an amplitude, a pulse width, a pulse rate, an electrode polarity, or an electrode combination associated with the stimulation.

27. The programming device of claim 15, further comprising a touch screen that includes one or more of the one or more input devices and one or more of the one or more output devices.

28. A system comprising:
   a medical device configured to deliver one or both of electrical signals or one or more therapeutic agents;
   a programming device configured to communicate with the medical device, the programming device comprising processing circuitry configured to:
      present, via a user interface (UI), a representation of the medical device and respective representations of each of a set of one or more components that are attachable to the medical device, wherein the set of components comprise at least one of leads, adaptors, extensions, or catheters;
      receive, via the UI, an indication of a selected component from the set of components for attachment to the medical device;
      responsive to receiving the indication of the selected component:
         select for presentation via the UI, respective indications of one or more compatible anatomical dropzones and one or more compatible port dropzones for the selected component, each respective anatomical dropzone representing an area on a representation of a patient body in which the selected component is implantable and each respective port dropzone representing a respective port either of the medical device or of a previously selected component attached to the medical device is compatible for connection with the selected component, wherein the previously selected component, if attached to the medical device, is either a distal bifurcator that bifurcates into two extension ports or a proximal bifurcator that combines into a single extension port;
         determine that the selected component has been dropped at a location of the UI that corresponds to the respective representation of a particular dropzone of the one or more compatible port dropzones;
         associate, based on the location of the UI that corresponds to the respective representation of the particular port dropzone in which the selected component was dropped, the selected component with a first port corresponding to the particular port dropzone either of the medical device or of the previously-selected component attached to the medical device;
         indicate, via the UI, attachment of the representation of the selected component to the representation of the medical device via the first port either of the medical device or of the previously selected component attached to the medical device;
         identify, based on the attachment of the selected component via the particular port of the medical device or of the previously selected component attached to the medical device, an updated set of one or more components that each has a configuration of electrical contact points attachable to the medical device with the attachment of the selected component via the particular port of the medical device or of the previously selected component attached to the medical device; and
         update the presentation of the respective representations of the set of one or more components via the UI to include only representations of the updated set of components that are attachable to the medical device with the attachment of the selected component via the first port either of the medical device or of the previously selected component attached to the medical device.

29. The system of claim 28, wherein the medical device is configured to deliver a combination of electrical stimulation and the one or more therapeutic agents using a catheter that includes one or more electrodes.

30. The system of claim 28,
wherein to present the representation of the medical device, the one or more processors of the programming device are configured to display the representation of the medical device in a first area of the UI,
wherein to present the respective representations of each of the set of components, the one or more processors are configured to display the respective representations of each of the set of components in a second area of the UI to include the representations of the updated set of components,
wherein to update the presentation of the respective representations of the set of components via the UI, the one or more processors are configured to update the second area of the UI, the one or more processors being further configured to present a third area of the UI,
wherein to receive the indication of the selected component for attachment to the medical device, the one or more processors are configured to receive user input that indicates repositioning of the representation of the selected component from the second area to the third area,
wherein to present the respective indications of the one or more compatible anatomical dropzones and the one or more compatible port dropzones, the processing circuitry is configured to present all of the respective indications in the third area, and
wherein to indicate attachment of the representation of the selected component to the representation of the medical device, the one or more processors are configured to indicate an attachment from the representation of the selected component in the third area to the representation of the medical device in the first area.

31. The system of claim 28, wherein the processing circuitry is further configured to:
select electrical stimulation programming options via the UI based on the configuration;
receive user input for programming delivery of the electrical signals by the medical device based on the selected stimulation programming options; and
program the medical device to deliver, to the patient body, the electrical signals according to the user input.

32. The system of claim 31, wherein to program the medical device to deliver the electrical signals according to the user input, the processing circuitry is configured to customize, based on the user input, one or more of an amplitude, a pulse width, a pulse rate, an electrode polarity, or an electrode combination associated of the electrical signals.

* * * * *